(12) United States Patent
Pattinson et al.

(10) Patent No.: US 10,696,034 B2
(45) Date of Patent: Jun. 30, 2020

(54) SYSTEMS, DEVICES, AND METHODS FOR DEPOSITION-BASED THREE-DIMENSIONAL PRINTING

(71) Applicant: Massachusetts Institute of Technology, Cambridge, MA (US)

(72) Inventors: Sebastian William Pattinson, Cambridge, MA (US); Anastasios John Hart, Waban, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/376,416

(22) Filed: Dec. 12, 2016

(65) Prior Publication Data
US 2017/0165908 A1    Jun. 15, 2017

Related U.S. Application Data

(60) Provisional application No. 62/266,082, filed on Dec. 11, 2015.

(51) Int. Cl.
*B29C 64/236* (2017.01)
*B33Y 10/00* (2015.01)
(Continued)

(52) U.S. Cl.
CPC ............ *B33Y 10/00* (2014.12); *B29C 64/106* (2017.08); *B29C 64/118* (2017.08); *B29C 64/20* (2017.08);
(Continued)

(58) Field of Classification Search
CPC ... B29C 64/118; B29C 64/209; B29C 64/232; B29C 64/236
See application file for complete search history.

(56) References Cited

U.S. PATENT DOCUMENTS 2,025,730 A    12/1935  Dickie et al.
2,053,766 A     9/1936  Dreyfus
(Continued)

FOREIGN PATENT DOCUMENTS

CN    103966761 A    8/2014
CN    104260357 A    1/2015
(Continued)

OTHER PUBLICATIONS

Ahn et al., Printed Origami Structures, Adv. Mater. 2010, 22, 2251-2254. (Year: 2010).*
(Continued)

*Primary Examiner* — Atul P. Khare
(74) *Attorney, Agent, or Firm* — Nutter McClennen & Fish LLP

(57) ABSTRACT

Methods, systems, and devices for extrusion-based three-dimensional printing are provided. The methods, systems, and devices allow for the printing materials such as fabrics, clothing, and wearable and/or implantable devices. A number of different enhancements are provided that allow for this improved form of three-dimensional printing, including: (1) printing using a polymer (e.g., cellulose acetate) dissolved in a solvent (e.g., acetone); (2) selectively bonding portions of a deposited filament onto one or more surfaces and/or one or more previously deposited filaments; (3) using particular toolpaths to create a fabric or similar material by creating a woven pattern; and (4) printing across multiple layers even when previous layers are not complete. Other aspects of the present disclosure, including other enhancements and various printer configurations, are also provided.

32 Claims, 7 Drawing Sheets

(51) Int. Cl.

| | | |
|---|---|---|
| *B29C 64/106* | (2017.01) | |
| *B29C 64/20* | (2017.01) | |
| *B29C 64/118* | (2017.01) | |
| *B29C 64/232* | (2017.01) | |
| *B29C 64/209* | (2017.01) | |
| *B33Y 30/00* | (2015.01) | |
| *B33Y 80/00* | (2015.01) | |
| *A61F 2/90* | (2013.01) | |
| *A61F 2/06* | (2013.01) | |
| *A61F 2/00* | (2006.01) | |
| *B29K 23/00* | (2006.01) | |
| *B29K 67/00* | (2006.01) | |
| *B29L 31/00* | (2006.01) | |

(52) U.S. Cl.
CPC ......... *B29C 64/209* (2017.08); *B29C 64/232* (2017.08); *B29C 64/236* (2017.08); *B33Y 30/00* (2014.12); *B33Y 80/00* (2014.12); *A61F 2/0063* (2013.01); *A61F 2/06* (2013.01); *A61F 2/90* (2013.01); *A61F 2210/0057* (2013.01); *A61F 2240/002* (2013.01); *A61F 2250/0012* (2013.01); *A61F 2250/0023* (2013.01); *B29K 2023/12* (2013.01); *B29K 2067/046* (2013.01); *B29L 2031/726* (2013.01); *B29L 2031/7534* (2013.01)

(56) References Cited

U.S. PATENT DOCUMENTS

| | | | |
|---|---|---|---|
| 2,825,625 A | 3/1958 | Hill et al. | |
| 3,012,925 A * | 12/1961 | Fry, Jr. | D01F 2/06 156/181 |
| 3,518,720 A * | 7/1970 | Fairbanks | B29C 48/30 425/71 |
| 3,525,785 A * | 8/1970 | Fairbanks | B29C 48/30 264/103 |
| 3,560,306 A * | 2/1971 | Nalle, Jr. | B29C 48/30 425/71 |
| 3,632,714 A * | 1/1972 | Fairbanks | B29C 48/30 264/103 |
| 3,782,872 A * | 1/1974 | Nalle, Jr. | B29C 48/30 425/131.1 |
| 3,844,874 A * | 10/1974 | Nalle, Jr. | B29C 48/30 428/127 |
| 3,949,111 A * | 4/1976 | Pelletier | B29C 65/04 428/109 |
| 4,144,368 A * | 3/1979 | Kim | B29D 28/00 428/105 |
| 4,194,249 A | 3/1980 | Thorneburg | |
| 4,304,234 A * | 12/1981 | Hartmann | D04H 3/007 604/372 |
| 4,323,525 A * | 4/1982 | Bornat | A61F 2/06 264/441 |
| 4,798,606 A * | 1/1989 | Pinchuk | A61F 2/06 623/1.1 |
| 5,121,329 A * | 6/1992 | Crump | B22F 3/115 228/180.5 |
| 5,501,824 A * | 3/1996 | Almquist | B29C 41/12 118/120 |
| 5,609,903 A * | 3/1997 | Israel | A21C 3/08 264/103 |
| 5,717,599 A | 2/1998 | Menhennett et al. | |
| 5,975,893 A | 11/1999 | Chishti et al. | |
| 7,569,273 B2 | 8/2009 | Bredt et al. | |
| 7,815,763 B2 * | 10/2010 | Fierens | A61F 2/91 156/167 |
| 8,463,418 B2 * | 6/2013 | Liu | B29C 64/106 700/119 |
| 9,003,643 B2 | 4/2015 | Munholand et al. | |
| 9,126,365 B1 * | 9/2015 | Mark | B29C 70/20 |
| 9,126,367 B1 * | 9/2015 | Mark | B29C 70/20 |
| 9,149,988 B2 * | 10/2015 | Mark | B29C 70/20 |
| 9,186,846 B1 | 11/2015 | Mark et al. | |
| 9,427,496 B2 * | 8/2016 | Sun | A61L 27/38 |
| 9,579,850 B2 | 2/2017 | Koreis | |
| 2005/0280184 A1 * | 12/2005 | Sayers | B29C 67/0059 264/308 |
| 2006/0204556 A1 | 9/2006 | Daniels et al. | |
| 2007/0170610 A1 * | 7/2007 | Payne | D04H 1/495 264/13 |
| 2009/0063717 A1 | 3/2009 | Bohm et al. | |
| 2009/0181104 A1 | 7/2009 | Rigotti et al. | |
| 2010/0256728 A1 * | 10/2010 | Rea Peterson | A61F 2/07 623/1.13 |
| 2010/0330144 A1 * | 12/2010 | Liu | B05B 13/0442 424/423 |
| 2012/0022646 A1 | 1/2012 | Mortarino et al. | |
| 2012/0150275 A1 * | 6/2012 | Shaw-Klein | A61F 2/88 623/1.15 |
| 2012/0190078 A1 | 7/2012 | Gatenholm et al. | |
| 2013/0238096 A1 | 9/2013 | Kotlus | |
| 2013/0317285 A1 * | 11/2013 | Soletti | A61L 27/507 600/36 |
| 2014/0268604 A1 | 9/2014 | Wicker et al. | |
| 2014/0272225 A1 * | 9/2014 | Johnson | A61L 27/14 428/36.1 |
| 2014/0272269 A1 * | 9/2014 | Hansen | D21F 1/0036 428/111 |
| 2014/0328964 A1 * | 11/2014 | Mark | B29C 70/20 425/166 |
| 2014/0358217 A1 | 12/2014 | Stankus et al. | |
| 2015/0048554 A1 | 2/2015 | Karrer et al. | |
| 2015/0056131 A1 | 2/2015 | Bemasconi et al. | |
| 2015/0102526 A1 | 4/2015 | Ward et al. | |
| 2015/0223928 A1 | 8/2015 | Limem et al. | |
| 2015/0246496 A1 | 9/2015 | Jones et al. | |
| 2015/0268485 A1 * | 9/2015 | Lussier | G02F 1/0131 359/291 |
| 2015/0335451 A1 | 11/2015 | Liu et al. | |
| 2016/0047075 A1 * | 2/2016 | Foley | D04H 1/728 264/465 |
| 2016/0346997 A1 * | 12/2016 | Lewis | B29C 67/0055 |
| 2017/0022111 A1 * | 1/2017 | Jarvis | B22F 3/1055 |

FOREIGN PATENT DOCUMENTS

| | | |
|---|---|---|
| CN | 104400999 A | 3/2015 |
| EP | 2 272 543 A2 | 1/2011 |
| WO | 2013/148719 A1 | 10/2013 |
| WO | 2014/153535 A2 | 9/2014 |
| WO | 2015/081996 A1 | 6/2015 |
| WO | 2015/120429 A1 | 8/2015 |

OTHER PUBLICATIONS

Nienhuijs, S.W., et al., An overview of the features influencing pain after inguinal hernia repair. Int J Surg. Aug. 2008;6(4):351-6. doi: 10.1016/j.ijsu.2008.02.005. Epub Mar. 4, 2008.

Northolt, M. G., "The structure and properties of cellulose fibres spun from an anisotropic phosphoric acid solution," Polymer, 2001, v. 42, pp. 8249-8264.

Novitsky, Y.W., Biology of biological meshes used in hernia repair. Surg Clin North Am. Oct. 2013;93(5):1211-5. doi: 10.1016/j.suc.2013.06.014. Epub Aug. 12, 2013.

Novitsky, Y.W., Bridging versus closing the defect during laparoscopic ventral hernia repair. Chapter 39, The SAGES Manual of Hernia Repair, Jacob, B.P., et al., eds., Springer Science+Business Media, New York, 2013, pp. 439-444.

Pickett, L.C., Prosthetic choice in open inguinal hernia repair. Chapter 2, The SAGES Manual of Hernia Repair, Jacob, B.P., et al., eds., Springer Science+Business Media, New York, 2013, pp. 19-26.

Poussier, M., et al., A review of available prosthetic material for abdominal wall repair. J Visc Surg. Feb. 2013;150 (1):52-9. doi: 10.1016/j.jviscsurg.2012.10.002. Epub Nov. 6, 2012.

Primus, F.E, et al., A critical review of biologic mesh use in ventral

(56) References Cited

OTHER PUBLICATIONS hernia repairs under contaminated conditions. Hernia. Feb. 2013;17(1):21-30. doi: 10.1007/510029-012-1037-8. Epub Jan. 8, 2013.
Qin, Z., et al., Structural optimization of 3D-printed synthetic spider webs for high strength. Nat Commun. May 15, 2015;6:7038. doi: 10.1038/ncomms8038. 7 pages.
Ralston, B. E , et al., "Viscosity of Soy Protein Plastics Determined by Screw-Driven Capillary Rheometry," J Polym Environ (2008) 16:169-176.
Rao, V.K., et al., Establishing a multidisciplinary academic cosmetic center. Plast Reconstr Surg. Dec. 2011;128 (6):741e-6e. doi: 10.1097/PRS.0b013e318222133a.
Resnick, A.S., et al., Surgeon contribution to hospital bottom line: Not all are created equal. Ann Surg. Oct. 2005;242 (4):530-7; discussion 537-9.
Reynolds, D., et al., Financial implications of ventral hernia repair: a hospital cost analysis. J Gastroint Surg. Jan. 2013;17(1):159-66; discussion p.166-7. doi: 10.1007/511605-012-1999-y. Epub Sep. 11, 2012.
Ricchetti, E.T., et al., Scaffold devices for rotator cuff repair. J Shoulder Elbow Surg. Feb. 2012;21(2):251-65. doi: 10.1016/j.jse.2011.10.003.
Rimdusit, S.; Jingjid, S.; Damrongsakkul, S. ; Tiptipakorn, S.; Takeichi, T. Biodegradability and Property Characterizations of Methyl Cellulose: Effect of Nanocompositing and Chemical Crosslinking. Carbohydr. Polym. 2008, 721 444-455.
Rosenblum, P., "Wet Seal Whipped: Expect More Casualties As Fast Fashion Retailers Take Over Teen Market," Forbes.com LLC, Jan. 20, 2015, 4 pages. Retrieved on Jul. 25, 2017 from <http://www.forbes.com/sites/paularosenblum/2015/01/20/fast-fashion-retailers-are-taking-over-the-teen-market/>.
Sanders, D., et al., An in vitro study assessing the effect of mesh morphology and suture fixation on bacterial adherence. Hernia. Dec. 2013;17(6):779-89. doi: 10.1007/510029-013-1124-5. Epub Jun. 19, 2013.
Sanders, D.L., et al., Mosquito net mesh for abdominal wall hernioplasty: a comparison of material characteristics with commercial prosthetics. World J Surg. Apr. 2013;37(4):737-45. doi: 10.1007/s00268-012-1900-x.
Shah, H.N., et al., Mesh complications in female pelvic floor reconstructive surgery and their management: A systematic review. Indian J Urol. Apr. 2012;28(2):129-53. doi: 10A103/0970-1591.98453.
Shridharani, S.M., et al., A systematic review of acelluar dermal matrices in head and neck reconstruction. Plast Reconstr Surg. Nov. 2012;130(5 Suppl 2):35S-43S. doi: 10.1097/PRS.0b013e31825eff7a.
Sittiwanchai, T.; Nakayama, I.; Inoue, S.; Jun, K. Transhumeral Prosthesis Prototype with 3D Printing and sEMG-Based Elbow Joint Control Method. Proc. 2014 Int. Cont. Adv. Mechatronic Syst., Kumamoto, Japan; Aug. 2014, 227-231.
Spinks, A., "Fast fashion's fickle market demands manufacturers closer to home," The Guardian, Guardian News and Media Limited, Dec. 11, 2014, 4 pages. Retrieved on Jul. 25, 2017 from <http://www.theguardian.com/sustainable-business/sustainable-fashion-blog/2014/dec/11/fast-fashions-fickle-market-demands-manufacturers-closer-to-home>.
Todros, S., et al., Biomechanical properties of synthetic surgical meshes for pelvic prolapse repair. J Mech Behav Biomed Mater. Mar. 2015;55:271-85. doi: 10.1016/jmbbm.2015.10.024. Epub Nov. 4, 2015.
U.S. Appl. No. 62/266,082, Systems, Devices, and Methods for Extrusion-Based Three-Dimensional Printing, filed Dec. 11, 2015 (75 pages).
Van Deventer, P.V., et al., Improving the longevity and results of mastopexy and breast reduction procedures: reconstructing an internal breast support system with biocompatible mesh to replace the supporting function of the ligamentous suspension. Aesthetic Plast Surg. Jun. 2012;36(3):578-89. doi: 10.1007/s00266-011-9845-2. Epub Nov. 20, 2011.
Wang, T.Y., et al., Contribution of plastic surgery to a health care system: our economic value to hospital profitability. Plast Reconstr Surg. Jan. 2012;129(1):154e-160e. doi: 10.1097/PRS.0b013e3182362b36.
Zbigniew, C. Z. Natural Polymer Man-Made Fibres; Academic Press Inc., New York, 1961.
Zhu, L.M., et al., Mesh implants: An overview of crucial mesh parameters. World J Gastrointest Surg. Oct. 27, 2015;7 (10):226-36. doi: 10.4240/wjgs.v7.i10.226.
[No Author Listed] 2014 Plastic Surgery Statistics Report. ASPS National Clearinghouse of Plastic Surgery Procedural Statistics, 2015, 23 pages.
[No Author Listed] "Abdominal Aortic Aneurysm Repair," The Univ. of Arizona Medical Center, The University of Arizona, 2013, 5 pages. As captured by the Internet Archive WayBackMachine on Jun. 17, 2014 from <https://web.archive.org/web/20140617171409/http://www.uahealth.com/library/sections/article/abdominal-aortic-aneurysm-repair>.
[No Author Listed] Artiste Medical Receives $4.6MM Investment to Support Development of Drug Eluting Hernia Mesh. Business Wire: A Berkshire Hathaway Company, Business Wire, Inc., Apr. 21, 2015, 2 pages. Retrieved on Jul. 24, 2017 from <http://www.businesswire.com/news/home/20150421006204/en/Ariste-Medical-Receives-4.6MM-Investment-Support-Development>.
[No Author Listed] Bio Skin Foot and Ankle Braces and Supports. Bio Skin, 2015, 2 pages. As captured by the Internet Archive WayBackMachine on Sep. 16, 2015 from <https://web.archive.org/web/20150916022559/http://www.bioskin.com/bio-skin-braces-and-supports/foot-and-ankle-braces-and-support/>.
[No Author Listed] Cellulose Acetate—A Global Strategic Business Report, Global Industry Analysts, Inc., <www.strategyr.com/Cellulose_Acetate_Market_Report.asp> originally accessed in 2011, 1 page.
[No Author Listed] "Electroloom—The World's First 3D Fabric Printer," Electroloom, on Kickstarter, PBC, launched May 15, 2015, 10 pages. Retrieved on May 12, 2017 from <https://www.kickstarter.com/projects/electroloom/electroloom-he-worlds-first-3d-fabric-printer>.
[No Author Listed] FDA stengthens requirements for surgical mesh for the transvaginal repair of pelvic organ prolapse to address safety risks. FDA News Release. FDA, U.S. Food & Drug Administration, U.S. Department of Health and Human Services, Jan. 4, 2016, 3 pages. Retrieved on Jul. 20, 2017 from <https://www.fda.gov/NewsEvents/Newsroom/PressAnnouncements/ucm479732.htm>.
[No Author Listed] Global Market for Hernia Repair Devices to Reach Valuation of US$5.93 bn by 2019. Transparency Market Research, Dec. 22, 2015, 4 pages. Retrieved on Jul. 20, 2017 from <http://www.transparencymarketresearch.com/pressrelease/hernia-repair-devices.htm>.
[No Author Listed] "Inventor Spotlight: Oluwaseyi Sosanya and his 3d Weaver Loom," Before It's News, Temporal Media, Inc., Jul. 4, 2014, 6 pages. Retrieved on May 12, 2017 from <http://beforeitsnews.com/science-and-technology/2014/07/inventor-spotlight-oluwaseyi-sosanya-and-his-3d-weaver-loom-2705410.html>.
[No Author Listed] Kugel Mesh Hernia Lawsuit Settlement Funding Amounts Increased at Legal-Bay Funding: Case Funding Firm to increase funding amounts on all settled Kugel mesh cases for plaintiffs who cannot wait to get their final payment. Cision PR Newswire, PR Newswire Association LLC, Legal-Bay LLC, Sep. 9, 2014, 2 pages. Retrieved on Jul. 20, 2017 from <http://www.prnewswire.com/news-releases/kugel-mesh-hernia-lawsuit-settlement-funding-amounts-increased-at-legal-bay-funding-274439981.html#>.
[No Author Listed] "Nike Debuts First-Ever Football Cleat Build Using 3D Printing Technology," Nike, Inc., Feb. 24, 2013, 3 pages. As captured by the Internet Archive WayBackMachine on Oct. 26, 2014 from <https://web-beta.archive.org/web/20141026092423/http://news.nike.com/news/nike-debuts-first-ever-football-cleat-built-using-3d-printing-technology/>.
[No Author Listed] Nike Free 3.0 Flyknit. Nike Free Running Shoes. Nike, Inc., 7 pages, 2016. As captured by the Internet Archive WayBackMachine on Mar. 6, 2016 from <https://web.archive.org/web/20160306122316/http://www.nike.com/us/en_us/c/running/free-3>.

(56) References Cited

OTHER PUBLICATIONS

[No Author Listed] "Other Positive Uses for Artificial Skin and Its Future," Mind Meets Matter: A Look at Some Novel Materials, Dickinson College, Nov. 21, 2010, 3 pages, As captured by the Internet Archive WayBackMachine on Jul. 9, 2013 from <https://web.archive.org/web/20130709231625/http://blogs.dickinson.edu:80/mindmeetsmatter/category/artificial-skin/>.

[No Author Listed] Permacol™ Surgical Implant., Covidien, 2014, 1 page. As captured by the Internet Archive WayBackMachine on Dec. 18, 2014 from <https://web.archive.org/web/20141218011625/http://www.covidien.com/surgical/products/hernia-repair/permacol-surgical-implant>.

[No Author Listed] PolyJet Technology: 3D print with precision in a wide range of materials. How PolyJet 3D Tinting Works. Stratasys Ltd, 3 pages. As captured by the Internet Archive WayBackMachine on Sep. 9, 2015, from <https://webarchive.org/web/20150909065012/http://www.stratasys.com/3d-printers/technologies/polyjet-technology>.

[No Author Listed] Selective laser sintering. Wikipedia, the free encyclopedia, Wikimedia Foundation, Inc., 4 pages. Retrieved on Jul. 25, 2017 from <https://en.wikipedia.org/wiki/Selective_laser_sintering>.

[No Author Listed] Shifting Paradigms: Fashion + Technology. Kent State University Museum, Kent State University, Sep. 26, 2013—Aug. 31, 2014, 1 page. As captured by the Internet Archive WayBackMachine on Apr. 23, 2015, from <http://web.archive.org/web/20150423102358/http://www2.kent.edu/museum/exhibits/exhibitdetail.cfm?customel_datapageid_2203427=3537053>.

[No Author Listed] Soft tissue repair market worth $14.7 billion in 2019. MarketsandMarkets, MarketsandMarkets Research Private Ltd., 2015, 2 pages. Retrieved from <http://www.marketsandmarkets.com/PressReleases/soft-issue-repair-devices.asp> on Jul. 20, 2017.

[No Author Listed] Stereolithography. Wikipedia, the free encyclopedia, Wikimedia Foundation, Inc., 4 pages. Retrieved on Jul. 25, 2017 from archived page of Aug. 28, 2015 <https://en.wikipedia.org/w/index.php?title=Stereolithography&oldid=678210838>.

[No Author Listed] Who Is SoftWear Automation. SoftWear Automation, Inc., 2014, 10 pages. As captured by the Internet Archive WayBackMachine on Apr. 7, 2015 from <https://web.archive.org/web/20150206001410/http://softwearautomation.com/about-us/>.

[No Author Listed] "Worlds First Fully 3D Printed Glasses by LUXeXceL," LUXeXceL Group BV, 3 pages. As captured py the Internet Archive WayBackMachine on Mar. 19, 2015, from <https://web.archive.org/web/20150319160412/https://www.luxexcel.com/news/3d-printed-glasses/>.

Alderman, A.K., et al., Financial impact of breast reconstruction on an academic surgical practice. Plast Reconstr Surg. May 2009;123(5):1408-13. doi: 10.1097/PRS.0b013e3181a0722d.

Aroori, S., et al., Chronic pain after hernia surgery—an informed consent issue. Ulster Med J. Sep. 2007;76 (3):136-40.

Abeer, M. M.; Amin, M. C. I. M; Martin, C., "A Review of Bacterial Cellulose-Based Drug Delivery Systems: Their Biochemistry, Current Approaches and Future Prospects," J. Pharm. Pharmacol. 2014, 66, 1047-1061.

Becker, H., et al., The use of synthetic mesh in reconstructive, revision, and cosmetic breast surgery. Aesthetic Plast Surg. Oct. 2013;37(5):914-21. doi: 10.1007/s00266-013-0171-8. Epub Jul. 17, 2013.

Bilsel, Y., et al., The search for ideal hernia repair; mesh materials and types. Int J Surg. 2012;10(6):317-21. doi: 10.1016/j.ijsu.2012.05.002. Epub May 12, 2012.

Bingham, G.A., et al., Efficient three dimensional modelling of additive manufactured textiles. Rapid Prototyping Journal, 2013, vol. 19, Issue 4, pp. 269-281.

Bjurstrom, M.F., et al., Pain control following inguinal herniorrhaphy: current perspectives. J Pain Res. May 29, 2014;7:277-90. doi: 10.2147/JPR.S47005. eCollection 2014.

Boland, T., et al., Application of inkjet printing to tissue engineering. Biotechnol J. Sep. 2006;1(9):910-7.

Bourell, D. L.; Watt, T. J.; Leigh, D. K.; Fulcher, B. Performance Limitations in Polymer Laser Sintering. Phys. Procedia 2014, 56, 147-156.

Bower, C., et al., Economics of abdominal wall reconstruction. Surg Clin North Am. Oct. 2013;93(5):1241-53. doi: 10.1016/j.suc.2013.06.007. Epub Jul. 30, 2013.

Breuing, K., et al., Incisional ventral hernias: review of the literature and recommendations regarding the grading and technique of repair. The Ventral Hernia Working Group. Surgery. Sep. 2010;148(3):544-58. doi: 10.1016/j. surg.2010.01.008. Epub Mar. 20, 2010.

Bringman, S., et al., Hernia repair: the search for ideal meshes. Hernia. Feb. 2010;14(1):81-7. doi: 10.1007/s10029-009-0587-x. Epub Dec. 11, 2009.

Brown, C.N., et al., Which mesh for hernia repair? Ann R Coll Surg Engl. May 2010;92(4):272-8. doi: 10.1308/003588410X12664192076296.

Burger, J.W., et al., Long-term follow-up of a randomized controlled trial of suture versus mesh repair of incisional hernia. Ann Surg. Oct. 2004;240(4):578-83; discussion 583-5.

Cai, D.; Song, M. Water-Based Polyurethane Filled with Multi-Walled Carbon Nanotubes Prepared by a Colloidal-Physics Method. Macromol. Chem. Phys. 2007, 208, 1183-1189.

Carey, M., et al., Vaginal surgery for pelvic organ prolapse using mesh and a vaginal support device. BJOG. Feb. 2008;115(3):391-7. doi: 10.1111/j.1471-0528.2007.01606.x.

Chao, A.H., et al., The differential impact of plastic surgery subspecialties on the financial performance of an academic clinical practice. Plast Reconstr Surg. Jun. 2014;133(6):748e-755e. doi: 10.1097/PRS.0000000000000174.

Chawla, P. R. et al., "Microbial Cellulose: Fermentative Production and Applications," Food Technol. Biotechnol. 47 (2) 107-124 (2009).

Chen, F. C. Effect of Entrance Geometry on the Capillary Flow of Cellulose Acetate Acetate-Acetone Solution. J. Appl. Polym. Sci. 1972, 16, 2175-2184.

Cosimo, Simon, Kinematics creates natural flowing 3D printed dress. www.3ders.org, 3D printer and 3D printing news, Dec. 9, 2014, 7 pages. Retrieved on Jul. 25, 2017 from <http://www.3ders.org/articles/20141209-kinematics-creates-natural-flowing-3d-printed-dress.html>.

Cui, X., et al., Human microvasculature fabrication using thermal inkjet printing technology. Biomaterials. Oct. 2009;30 (31):6221-7. doi: 10.1016/j.biomaterials.2009.07.056. Epub Aug. 19, 2009.

D'Aveni, R. The 3-D Printing Revolution. Harv. Bus. Rev. 2015, 40-48.

De Bruijn, H.P., et al., Mastopexy with 3D preshaped mesh for long-term results: development of the internal bra system. Aesthetic Plast Surg. Sep. 2008;32(5):757-65. doi: 10.1007/500266-008-9186-y. Epub May 21, 2008.

Deerenberg, E.B., et al., Experimental study on synthetic and biological mesh implantation in a contaminated environment. Br J Surg. Dec. 2012;99(12):1734-41. doi: 10.1002/bjs.8954.

Dieterich, M., Heterologous breast reconstruction using a titanium-coated polypropylene mesh (TiLOOP® Bra). Breast Reconstruction, Shiffman, M, ed., Springer International Publishing, 2016, Chapter 34, pp. 391-398.

Doctor, H.G., Evaluation of various prosthetic materials and newer meshes for hernia repairs. J Minim Access Surg. Sep. 2006;2(3):110-6.

Engelsman, A.F., et al., The phenomenon of infection with abdominal wall reconstruction. Biomaterials. May 2007;28(14):2314-27. Epub Feb. 2, 2007.

Falagas, M.E., et al., Mesh-related infections after hernia repair surgery. Clin Microbiol Infect. Jan. 2005;11(1):3-8.

Falagas, M.E., et al., Mesh-related infections after hernia repair. Hernia Repair Sequelae, Schumpelick, V., et al., ads., Springer-Verlag GmbH, 2010, Chapter 13, pp. 97-102.

Faruk, O., et al., "Biocomposites reinforced with natural fibers: 2000-2010," Progress in Polymer Science, 2012, v. 37, pp. 1552-1596.

Faulkner, H.R., et al., Three Years Experience with Absorbable Mesh in Single-Stage Breast Reconstruction: A Cost-Effective Alter-

(56) References Cited

OTHER PUBLICATIONS native. Plast Reconstr Surg. Oct. 2015;136(4 Suppl):112-3. doi: 10.1097/01.prs.0000472419.12175.cb.
Flum, D.R., et al., Have outcomes of incisional hernia repair improved with time? A population-based analysis. Ann Surg. Jan. 2003;237(1):129-35.
Ganster, J., et al., "Novel cellulose fibre reinforced thermoplastic materials," Cellulose (2006) 13:271-280.
Gerratt, A. P.; Michaud, H. O.; Lacour, S.P., "Elastomeric Electronic Skin for Prosthetic Tactile Sensation," Adv. Funct. Mater. 2015, 25, 2287-2295.
Gladman, A.S., et al., Biomimetic 4D printing. Nat Mater. Apr. 2016;15(4):413-8. doi: 10.1038/nmat4544. Epub Jan. 25, 2016.
Gou, M.; Qu, X.; Zhu, W.; Xiang, M.; Yang, J.; Zhang, K.; Wei, Y.; Chen, S. Bio-Inspired Detoxification Using 3D Printed Hydrogel Nanocomposites. Nat. Commun. 2014, 5, pp. 1-9.
Halterman, T. E., "American Process and ORNL Say Nanocellulose Will Rival Carbon Fiber for 3D Printing," May 28, 2015, 4 pages, <https://3dprint.com/69012/american-process-and-oml-say-nanocellulose-will-rival-carbon-fiber-for-3d-printing/>.
Ho, G., et al., A systematic review and meta-analysis of complications associated with acellular dermal matrix-assisted breast reconstruction. Ann Plast Surg. Apr. 2012;68(4):346-56. doi: 10.1097/SAP.0b013e31823f3cd9.
Hollinsky, C., et al., Measurement of the tensile strength of the ventral abdominal wall in comparison with scar issue. Clin Biomech (Bristol, Avon). Jan. 2007;22(1):88-92. Epub Aug. 10, 2006.
Hollinsky, C., et al., Comparison of a new self-gripping mesh with other fixation methods for laparoscopic hernia repair in a rat model. J Am Coll Surg. Jun. 2009;208(6):1107-14. doi: 10.1016/tjamcollsurg.2009.01.046. Epub Apr. 17, 2009.
Hong, S.; Sycks, D.; Chan, H. F.; Lin, S.; Lopez, G. P.; Guilak, F.; Leong, K. W.; Zhao, X., 3D Printing of Highly Stretchable and Tough Hydrogels into Complex, Cellularized Structures. Adv. Mater. 2015, v. 27, pp. 4035-4040.
Huang, S. H.; Liu, P.; Mokasdar, A.; Hou, L. Additive Manufacturing and Its Societal Impact: A Literature Review. Int. J. Adv. Manuf. Technol. 2013, 67, 1191-1203.
Huber, T. et al., "A critical review of all-cellulose composites," J. Mater. Sci., 2012, v. 47, p. 1171-1186.
Ifkovits, J.L., et al., Review: photopolymerizable and degradable biomaterials for tissue engineering applications. Tissue Eng. Oct. 2007;13(10):2369-85.
Invitation to Pay Additional Fees for Application No. PCT/US16/66205, mailed Feb. 13, 2017. (2 pages).
International Search Report and Written Opinion for Application No. PCT/US16/66205, dated Apr. 14, 2017 (11 pages).
Irgens, F., Rheology and Non-Newtonian Fluids; Springer International Publishing, Switzerland, 2014, 192 pages.
Ivanova, O., et al., Additive Manufacturing (AM) and Nanotechnology: Promises and Challenges. 22nd Annual International Solid Freeform Fabrication (SFF) Symposium, Aug. 8-10, 2011, University of Texas, Austin, Texas, pp. 733-749.
Jelovsek, J.E., et al., Pelvic organ prolapse. Lancet. Mar. 24, 2007;369(9566):1027-38.
Johnson, A., et al., Additive manufactured textiles for high-performance stab resistant applications. Rapid Prototyping Journal, 2013, vol. 19, Issue 3, pp. 199-207.
Kim, S-Y, et al., "Investigation of Size Effect on Film Type Haptic Actuator Made with Cellulose Acetate," Smart Mater. Struct. 2014, 23, 045016, pp. 1-6.
Kingsnorth, A., et al., Hernias: Inguinal and incisional. The Lancet, 2003, vol. 362, pp. 1561-1571.
Klemm, D. et al., "Cellulose: Fascinating Biopolymer and Sustainable Raw Material," Angew. Chem. Int. Ed., 2005, v. 14, pp. 3358-3393.
Klinge, U., et al., Influence of polyglactin-coating on functional and morphological parameters of polypropylene-mesh modifications for abdominal wall repair. Biomaterials. Apr. 1999;20(7):613-23.
Klinge, U., et al., Functional and morphological evaluation of a low-weight, monofilament polypropylene mesh for hernia repair. J Biomed Mater Res. 2002;63(2):129-36.
Koski, M.E., et al., Implications of the FDA statement on transvaginal placement of mesh: the aftermath. Curr Urol Rep. Feb. 2014;15(2):380. doi: 10.1007/s11934-013-0380-3.
Krassenstein, E., "Little girl born without a nose has one built for her thanks to 3D printing," 3DPrintBoard.com, #DR Holdings, LLC, Jun. 3, 2015, 5 pages. Retrieved on May 12, 2017 from <http://3dprint.com/70437/3d-printed-nose-little-girl/>.
Kruth, J.P.; Froyen, L.; Van Vaerenbergh, J.; Mercelis, P.; Rombouts, M.; Lauwers, B. Selective Laser Melting of Iron-Based Powder J. Mater. Process. Technol. 2004, 149, 616-622.
Kuhlmann-Capek, M.J., et al., Enmeshed in Controversy: Use of Vaginal Mesh in the Current Medicolegal Environment. Female Pelvic Med Reconstr Surg. Sep.-Oct. 2015;21(5):241-3. doi: 10.1097/SPV.0000000000000192.
Kulah, B., et al., Presentation and outcome of incarcerated external hernias in adults. Am J Surg. Feb. 2001;181 (2)101-4.
Kulshreshtha, A. K., et al., "A variance analysis of the line broadening of x-ray profiles from Fortisan," Polymer, 1973, v 14, pp. 402-404.
Kevin, L.S., The business of academic plastic surgery. Plast Reconstr Surg. Jul. 2010;126(1):303-7. doi: 10.1097/PRS.0b013e3181dbc0af.
Li, R.; Liu, J.; Shi, Y.; Wang, L.; Jiang, W. Balling Behavior of Stainless Steel and Nickel Powder during Selective Laser Melting Process. Int. J. Adv. Manuf. Technol. 2012, 59, 1025-1035.
Lussenburg, K., et al., Designing with 3D printed textiles: A case study of material driven design. iCAT 2014. Proceedings of 5th International Conference on Additive Technologies, 2014, pp. 74-81.
MacAdam, S.A., et al., Acellular dermal matrices: Use in reconstructive and aesthetic breast surgery. Can J Plast Surg. 2012 Summer;20(2):75-89.
Maher, C., et al., Surgical management of pelvic organ prolapse in women (Review). Cochrane Database of Systematic Reviews, 2013, Issue 4, Article No. CD004014, 4 pages, DOI: 10.1002/14651858. CD004014.pub5.
Markstedt, K., et al., 3D Bioprinting Human Chondrocytes with Nanocellulose-Alginate Bioink for Cartilage Tissue Engineering Applications. Biomacromolecules. May 11, 2015;16(5):1489-96. doi: 10.1021/acs.biomac.5b00188. Epub Apr. 7, 2015.
Martson, M.; Viljanto, J.; Hurme, T.; Laippala, P.; Saukko, P. Is Cellulose Sponge Degradable or Stable as Implantation Material? An in Vivo Subcutaneous Study in the Rat. Biomaterials 1999, 20, 1989-1995.
Melchels, F. P. W.; Feijen, J.; Grijpma, D. W. A Review on Stereolithography and Its Applications in Biomedical Engineering. Biomaterials2010, 31, 6121-6130.
Melnikova, R. et al."3D printing of textile-based structures by Fused Deposition Modelling (FDM) with different Polymer materials" 2014 IOP Conference Series: Materials Science and Engineering, vol. 62, Publication [online]. May 24-27, 2014. [Retrieved Mar. 23, 2017). <url:http://iopscienceiop.org/article/10.1088/1757-899X/62/1/012018/pdf>; 012018/pdf>; <doi:10.1088/1757-899X/62/1/012018>;.
Mital, R., Imports continue to dominate Indian medical textiles markets. Technical Textiles International, International Newsletters Ltd., Jun. 2007, pp. 47-50, [http://www.technical-textiles.net/news/imports-continue-dominate-indian-medical-textiles-markets].
Millsaps, B.B., Picsima Technology 3D Prints Directly with Silicone, May Completely Transform the Breast Implant Industry. 3DPrint.com: The Voice of 3D Printing / Additive Manufacturing, 3DR Holdings, LLC, May 21, 2015, 4 pages. Retrieved on Jul. 24, 2017 from <https://3dprint.com/67111/picsima-3d-prints-silicone/.
Miyamoto, T.; Takahashi, S.; Ito, H.; Inagaki, H.; Noishiki, Y. Tissue Biocompatibility of Cellulose and Its Derivatives. J. Biomed. Mater. Res. 1989, 23, 125-133.
Mohamed, O. A..; Masood, S. H.; Bhowmik, J. L., Optimization of Fused Deposition Modeling Process Parameters: A Review of Current Research and Future Prospects. Adv. Manuf. 2015, v. 3, 42-53.

(56) References Cited

OTHER PUBLICATIONS

Moon, R. J. et al., "Cellulose nanomaterials review: structure, properties and nanocomposites," Chem. Soc. Rev., 2011, 40, 3941-3994.

Mucowski, S.J., et al., Use of vaginal mesh in the face of recent FDA warnings and litigation. Am J Obstet Gynecol. Aug. 2010;203(2):103.e1-4. doi: 10.1016/j.ajog.2010.01.060. Epub Mar. 15, 2010.

Muller, F. a.; Muller, L.; Hofmann, L; Greil, P.; Wenzel, M. M.; Staudenmaier, R., Cellulose-Based Scaffold Materials or Cartilage Tissue Engineering. Biomaterials 2006, 27, 3955-3963.

Nahabedian, M.Y., Achieving ideal donor site aesthetics with autologous breast reconstruction. Gland Surg. Apr. 2015;4(2):145-53. doi: 10.3978/j.issn.2227-684X.2015.02.04.

Narat, J., K, et al., "Repair of Abdominal Wall Defects with Fortisan Fabric; Experimental Study," Ann. Surg. 1952, 136, 272-277.

Extended European Search Report for 16874061.1 dated Jul. 16, 2019 (8 pages).

\* cited by examiner

SYSTEMS, DEVICES, AND METHODS FOR DEPOSITION-BASED THREE-DIMENSIONAL PRINTING

CROSS REFERENCE TO RELATED APPLICATION

The present disclosure claims priority to U.S. Provisional Application No. 62/266,082, entitled "Systems, Devices, and Methods for Extrusion-Based Three-Dimensional Printing," which was filed on Dec. 11, 2015, and which is incorporated by reference herein in its entirety.

GOVERNMENT RIGHTS

This invention was made with Government support under Grant No. SMA-1415129 awarded by the National Science Foundation. The Government has certain rights in the invention.

FIELD

The present disclosure relates to systems, devices, and methods for three-dimensional printing, and more particularly relates to deposition-based (e.g., extrusion-based) processes, systems, and devices to additively manufacture materials with controlled strength and flexibility, such as fabrics and other materials that can comfortably fit contoured surfaces.

BACKGROUND

Medical textiles are often used in surgeries where tissues need to be covered, connected, or held in place, which is common in sports medicine, as well as cardiovascular, orthopedic, bariatric, and cosmetic surgeries, among others. Soft tissue repair surgeries are extremely common as every year there are an estimated 1 million hernia repair surgeries, 300,000 pelvic organ prolapse repairs, 260,000 stress urinary incontinence surgeries, 300,000 breast reconstructions/augmentations, and ~55,000 rotator cuff repairs in the United States. The most prominent examples of treatments that depend on medical textiles include hernia repair, in which a textile can hold protruding tissue in place, aortic grafts to repair blood vessels, artificial skin grafts to cover burnt skin, braces to immobilize sprained ankles, and compression stockings or hosiery to improve circulation. Mesh (typically knitted/woven synthetic polymer) is commonly used to mechanically support tissue as it heals and to reduce injury recurrence rates because it can allow for a tension-free repair.

Many patients suffer serious complications after mesh implantation, as existing meshes can weaken and irritate body tissues. For example, 25% of abdominal hernias recur within three years because mesh migrates or abdominal tissue does not heal, up to 43% of hernia patients experience chronic pain, and 10% of hernia patients suffer infections requiring mesh replacement. Many complications are caused by mismatches between mesh, which is typically flat with a uniform mechanical stiffness, and human tissue, which can have great variation in properties such as curvature, stiffness, and direction of motion within a single patient, and across similar locations for different patients. Items worn on or in the human body, ranging from clothing and eyeglasses to prostheses and medical implants, typically are fitted to the person that wears it for the item to be effective for that individual. Similarly, meshes work better, whether in terms of comfort, aesthetics, or other function, when their geometry is tailored to the user. Currently, such tailoring is accomplished by: 1) producing various standard sizes; 2) making the device size adjustable, for example through clasps or straps; and 3) by bespoke tailoring, where these items are individually handmade to measurements of a person. The first two of these only imperfectly approximate different body shapes, while bespoke tailoring is prohibitively expensive for the vast majority of applications.

Three-dimensional ("3D") printing is growing in popularity as a way to produce objects, including but not limited to medical implants. There are multiple known techniques for printing three-dimensionally, such as non-extrusion based processes like stereolithography and PolyJet processing, and extrusion-based processes like fused deposition modeling (FDM). While these techniques do offer benefits, such as allowing for high resolution printing, they suffer from a number of shortcomings as well. For example, many objects printed using known, traditional 3D-printing techniques produce parts that have significantly poorer mechanical properties than those produced by traditional fiber composite manufacturing processes. This is at least because the existing 3D-printing techniques are not as adaptable or configurable to easily provide a variety of properties across a surface area of the printed object (e.g., it is difficult to change the strength and/or flexibility of a printed object across a surface area of the object). Most 3D-printing materials are either hard and stiff, and thus difficult to conform to surfaces and uncomfortable to wear, or they are mechanically fragile. The latter is true particularly for materials printed that are intended to be biocompatible, such as hydrogels (~200 kPA tensile strength).

One example of a 3D printing technique that does not provide strength and flexibility that is often desirable for an object to have is a technique known as selective laser sintering (SLS). During an SLS printing process, a roller distributes powder in layers that are then partially melted by a laser to induce bonding in a pattern. This process can print metals and is relatively rapid, but its mechanical properties tend to be relatively poor due to residual thermal stresses and porosity, as well as the machines being relatively expensive to buy and run.

Additive manufacturing generally refers to manufacturing a part by adding material as opposed to subtracting, and thus is a way by which parts can be printed three-dimensionally. Additive manufacturing techniques include some of the aforementioned techniques (e.g., FDM), as well as others, such as fused filament fabrication (FFF). This technique is different from other 3D-printing techniques because it allows deposited material to be added on top of and bonded to previously deposited material rather than relying upon an existing mold or subtracting material from a mass of material to produce a 3D-object. Additive manufacturing is growing in popularity as a 3D-printing technique because it allows users to create unique geometries and process unique material compositions. However, even existing additive manufacturing 3D-printing techniques are limited in their ability to print a variety of materials, at a desirable manufacturing rate, and at a desirable manufacturing cost. Further, even existing additive manufacturing 3D-printing techniques suffer from similar deficiencies as other 3D-printing techniques when it comes to printing objects that are adaptable or configurable to easily provide a variety of properties across a surface area of the printed object. For example, even using existing additive manufacturing 3D-printing techniques, it is still difficult to change the strength and/or flexibility of a printed object, such as a surgical mesh, across a surface area of the object. Generally, fabrics and the like produced using existing additive manufacturing 3D-printing techniques are of significantly poorer quality than those produced by traditional fiber compositing manufacturing processes. This is at least because existing additive manufacturing 3D-printing techniques result in poorer molecular alignment along a fiber axis and issues related achieving strong inter-layer bonding. Still further, additively manufactured parts typically have a relatively homogenous structure, most simply featuring isotropic or uncontrolled anisotropic bonding, which makes parts brittle and stiff, and thus unsuitable for wear.

Accordingly, there remains a need to improve methods, systems, and devices for producing 3D-printed parts that allow the parts to be printed to have a desirable strength and flexibility, thereby allowing the printed parts to be adaptable or customizable as desired. While the present disclosures are by no way limited to 3D-printed parts in the medical field, within that field there is a need for improved methods, systems, and devices for producing 3D-printed medical components (e.g., medical textiles and medical implants), by way of non-limiting example, surgical meshes for soft tissue repair surgeries, that have a desirable strength and flexibility for use in various surgical procedures and that can be customized and configured based on the needs of a patient and/or surgical procedure, and/or the preferences of a surgeon or other clinician.

SUMMARY

The present disclosure generally relates to deposition-based (e.g., extrusion-based) three-dimensional printing methods, systems, and devices, and it provides for a number of different advances in three-dimensional printing. Each of the advances, by themselves and in any combination, allows for the printing of materials such as fabrics, packaging, clothing, and wearable and/or implantable devices. The present disclosure highlights some of these advances with more particularity than others, although such highlighting by no means indicates the inventive nature of one advance or aspect in comparison to another. A person skilled in the art, in view of the present disclosure, will be able to determine numerous advances, and combinations of advances, that represent inventive subject matter.

In one exemplary embodiment of a method for printing in three dimensions, the method includes depositing a filament onto at least one of a surface and one or more previously deposited filaments, and modulating adhesion of the filament to the at least one of the surface and the one or more previously deposited filaments across a length of the filament to form a fabric.

In some embodiments the filament contacts but is unbonded with respect to the surface and/or the previously deposited filament(s) in one or more locations along a length of the surface and/or the previously deposited filament(s). The fabric can have a varied mechanical response that can result from configuration of the fabric in which a first region across a surface area of the fabric has smaller pores formed between one or more deposited filaments than pores formed between one or more deposited filaments of a second region across the surface area of the fabric. The filament can include at least one of a continuous, pre-made filament, an adhesive-coated filament, and an adhesive filament. In some embodiments, the surface onto which the filament is deposited is an adhesive surface.

A number of ways by which adhesion can be modulated are provided for herein or are otherwise derivable from the present disclosures. For example, modulating adhesion can include performing photopolymerization on a bonding agent that is in contact with the deposited filament. Other examples include: (1) bringing the filament into contact with the surface and/or the previously deposited filament(s); (2) controlling a rate at which a solvent associated with the filament evaporates prior to the filament coming into contact with the surface and/or the previously deposited filament(s); (3) selectively exposing regions before, during, or after depositing the filament to light able to cure a photopolymer, or a material having light-responsive bonding agents associated therewith; (4) selectively exposing regions to heat before, during, or after depositing the filament; (5) selectively using an adhesive at regions before, during, or after depositing the filament; and (6) selectively using an adhesive to provide bonding between the filament and the previously deposited filament(s). In some instances, modulating adhesion can include controlling one or more of the following fabric properties: deformation, electrical conductivity, thermal conductivity, and toughness. Modulating adhesion of the filament using the techniques provided for herein can control a shear modulus of the fabric.

The method can further include depositing one or more additional filaments onto at least one of a surface and one or more previously deposited filament, and likewise modulating adhesion of the one or more additional filaments to the at least one of the surface and the one or more previously deposited filaments across a length of the one or more additional filaments. In such instances, the method can also include locally adjusting at least one of an orientation, thickness, and composition of at least one of: (a) the deposited filament(s); and (b) one or more adhesives used in conjunction with the one or more deposited filament(s), such that the fabric has a varied mechanical response to application of an outside force across a surface area of the fabric. Locally adjusting at least one of the orientation, thickness, and composition of the deposited filament and/or the adhesive(s) used in conjunction with the deposited filament(s) can further include: (1) modulating shear stress of the fabric by changing interfilament bonding; (2) modulating out-of-plane extension of the fabric in response to in-plane compression or tension of the fabric; (3) modulating tensile stiffness of the fabric through localized filament slack; and (4) modulating Poisson's ratio through filament and bonding patterns.

Many different materials can be used in conjunction with the above-discussed methods. For example, the material of the deposited filament(s) and/or the material of one or more adhesives used in conjunction with the filament(s) can include either or both of a thermoplastic polymer and a thermoset polymer, among other materials. In some embodiments, the filament and an adhesive used in conjunction with the filament can be the same material.

The method can further involve dissolving a polymer in a solvent to form a viscous fluid. In such instances, the step of depositing a filament onto at surface and/or previously deposited filament(s) can include extruding the viscous fluid through a nozzle to form the filament. Many different ways by which a filament can be extruded are provided in the present disclosure. In some embodiments, steps related to extruding can include a step that is sometimes referred to in the present disclosure as stretching. For example, extruding the viscous fluid through a nozzle to form a filament can include positioning the nozzle at a first location with respect to the surface and/or previously deposited filament(s) and depositing an initial portion of the filament from the nozzle at a first site on the surface and/or previously deposited filament(s). The process can continue by moving the nozzle to a second location with respect to the surface and/or the previously deposited filament(s) while depositing an additional portion of the filament from the nozzle towards the surface and/or the previously deposited filament(s) to stretch the additional portion of the filament. Still further, the process can continue by positioning the nozzle at a third location with respect to the surface and/or the deposited filament(s) and depositing an end portion of the filament from the nozzle at a second site on the surface and/or the previously deposited filament(s).

In some embodiments that involve stretching, moving the nozzle to a second location can also include the action of raising the nozzle to the second location with the second location being above the first location with respect to the surface and/or the previously deposited filament(s). The nozzle can also be accelerated when it is being raised to the second location. In some instances, regardless of whether the nozzle is raised when moving to the second location, the nozzle can be accelerated after positioning the nozzle at a third location to straighten the additional portion of the filament. The first and third location as defined more generally by the method can both be proximate to the surface.

One exemplary embodiment of a garment, medical textile, or medical implant includes a plurality of filaments disposed with respect to each other to form a non-woven fabric that has a plurality of intersection locations at which a portion of one filament of the plurality of filaments intersects another filament of the plurality of filaments. The filaments at one or more intersection locations of the plurality of intersection locations are bonded together, while the filaments at one or more other intersection locations of the plurality of intersection locations are not bonded together. The one or more intersection locations that are bonded together are non-stochastically and rationally distributed with respect to a volume of the garment, medical textile, or medical implant.

The garment, medical textile, or medical implant can be configured such that when it is laid out with no folds or wrinkles onto a planar surface, the garment, medical textile, or medical implant conforms to the non-planar surface. The non-woven fabric can be devoid of interstices between the filaments that are bonded together. In some embodiments, the properties of the non-woven fabric can be impacted by changing a patterning of at least one of the filaments and an adhesive used in conjunction with the filaments, with respect to other filaments or other adhesives used in conjunction with the filaments. In some embodiments, the properties of the non-woven fabric can be impacted by changing a composition of at least one of the filaments and an adhesive used in conjunction with the filaments in a first region of the fabric while not necessarily changing a composition of at least one of the filaments and an adhesive used in conjunction with the filaments in a second region of the fabric.

A first region across a surface area of the non-woven fabric can have smaller pores formed between one or more filaments than pores formed between one or more filaments of a second region across the surface area of the garment, medical textile, or medical implant. In some embodiments, a diameter of filament of the plurality of filaments can be at least about 200 microns. In some instances, the garment, medical textile, or medical implant is a surgical mesh, such as one that can be used to treat hernias, while in other instances, the garment, medical textile, or medical implant is a stent that is configured to change to a predetermined and customized shape based on a configuration of the plurality of filaments and/or any adhesive of the non-woven fabric.

In another exemplary embodiment of a method for printing in three dimensions, the method includes dissolving a polymer that includes cellulose acetate in a solvent to form a viscous fluid, extruding the viscous fluid through a nozzle to form a filament, and depositing the filament onto a surface in layers to form a three-dimensional part.

In some embodiments, the solvent includes acetone. The method can also include a step of controlling a level of adhesion by the filament to at least one of the surface, one or more other surfaces, and one or more deposited filaments. Controlling a level of adhesion by a filament can be achieved, for example, by adjusting a distance between the nozzle and the at least one of the surface, the one or more other surfaces, and the one or more deposited filaments onto which the filament is deposited. Other methods for controlling a level of adhesion are also provided in the present disclosure, and include: (1) adjusting a concentration of the solvent, and (2) adjusting a rate at which the viscous fluid is deposited out of the nozzle. The surface onto which the filament is deposited can be a three-dimensional template, and the deposited filament can substantially conform to the shape of the three-dimensional template.

The method can further include depositing a plurality of filaments onto at least one of the surface, one or more other surfaces, and one or more deposited filaments. Each filament of the plurality of filaments can be formed by extruding the viscous fluid through the nozzle. In some embodiments, a stretching step can be utilized for at least one of the steps of depositing filament onto a surface and depositing a plurality of filaments onto at least one of the surface, one or more other surfaces, and one or more deposited filaments. For example, the method can include positioning the nozzle at a first location in space to deposit an initial portion of the filament at a first site on the surface, on one or more other surfaces or on one or more deposited filaments onto which the filament is being deposited. The nozzle can be raised to a second location in space that is above the first location while depositing an additional portion of the filament on the surface, on one or more other surfaces, or on one or more deposited filaments onto which the filament is being deposited. Still further, the nozzles can be positioned at a third location in space to deposit an end portion of the filament at a second site on the surface, on one or more other surfaces, or on one or more deposited filaments onto which the filament is being deposited. In some embodiments, in addition to raising the nozzle to a second location, the nozzle can be accelerated. Further, in some instances, regardless of whether the nozzle is raised when moving to the second location, the nozzle can be accelerated after positioning the nozzle at a third location to straighten the additional portion of the filament. The first and third location as defined more generally by the method can both be proximate to the surface.

In some aspects, the present disclosure provides for methods, systems, and devices that print three-dimensionally by using a polymer dissolved in a solvent. Dissolving the polymer in the solvent can form a viscous fluid, sometimes referred to as "dope." While and/or after the viscous fluid is ejected out of one or more print nozzles, the solvent evaporates, leaving the polymer in filament form. In some instances, a filament can stop being adhesive once the solvent evaporates. A combination of deposited filaments results in a three-dimensionally printed object. Many examples of three-dimensionally printed objects are provided for herein, including but not limited to fabrics, clothing, wearable devices, and implantable devices. In some instances in the present disclosure, reference to ejecting or depositing a viscous fluid or dope is used interchangeably with reference to ejecting or depositing a filament since the result of ejecting the dope is a filament. A person skilled in the art will understand this interchangeable use, and as such, reference to ejecting or depositing a filament can include ejecting or depositing a material, such as dope, that will eventually become a filament.

The rate at which the solvent evaporates can be controlled, thereby allowing for different configurations and characteristics of the printed material. The rate can be controlled by adjusting a number of different parameters, including but not limited to a distance between a depositing end of a nozzle and a surface or other object (including a previously deposited filament) onto which the dope is printed, a concentration of the solvent, the nozzle temperature, the deposition chamber temperature, and a rate at which the dope is deposited out of the nozzle. The dope, and thus ultimately the filament, can be deposited on any number of surfaces, including a flat surface, a contoured surface, previously deposited fluid/filament, etc. In some instances, the surface can be a three-dimensional template, to which the deposited filament can substantially conform, thereby taking the shape of the three-dimensional template.

In some exemplary embodiments, the polymer includes cellulose acetate and the solvent includes acetone. A person skilled in the art, in view of the present disclosure, can recognize other polymers and solvents that can be used in conjunction with the present disclosures. Performing chemical reactions, such as hydrolysis, on the deposited filament can further strengthen or harden the filament, or provide diverse other characteristics such as hydrophilicity, by replacing the molecules on the cellulose acetate molecule. By way of non-limiting example, when hydrolysis is performed on cellulose acetate, the resulting material can be cellulose. It is also possible to produce diverse other cellulose derivatives by this method, including carboxymethyl cellulose and methylcellulose. Some exemplary, non-limiting materials that can be used in conjunction with performing chemical modifications, such as hydrolysis, include sodium hydroxide and phosphoric acid. A person skilled in the art, in view of the present disclosures, will recognize how a system or device, such as a printer, can be made or otherwise adapted for use with polymers and solvents such as cellulose acetate and acetone, as well as various features that can be included as part of the systems and devices to operate and/or enhance the performance of the same. Such adaptations will depend, for example, on the material used as the dope. By way of non-limiting example, if the system includes cellulose acetate in acetone, a storage container of the system or device can be gas tight, while a printing chamber can be well-ventilated. The printing chamber could also be heated or cooled to modulate the drying kinetics. For other dopes, or other filament sources such as thermoplastics, conditions related to limiting water vapor may be important. Still further, an antibiotic agent, photocurable material, electrically conductive additive, or other functional component can be included as part of any deposited material, and then an interaction can be initiated, to further enhance the properties and capabilities of the deposited material. This can be useful, for example, when the printed material is used in conjunction with an implantable medical device.

In some other aspects, the present disclosure provides for methods, systems, and devices that control whether or not particular portions of a deposited filament bond to a surface or other object (including a previously deposited filament; to the extent the term "other object" is used herein, it typically also includes a previously deposited filament, unless otherwise specified) upon extrusion. A number of different parameters can be monitored and controlled to impact whether a bond is formed, including but not limited adjusting a distance between a depositing end of a nozzle through which dope that forms the filament is deposited and a surface or other object onto which the filament becomes disposed, a concentration level of a solvent used in forming the dope, and the rate at which the dope is deposited out of the nozzle. Furthermore, the bonding can also be controlled for printing materials that are not polymers dissolved in solvent. Non-limiting examples of these include thermoplastic polymers, photopolymers, thermoset polymers, and pre-made continuous, semi-continuous, or non-continuous fibers that are mixed with a material that can be made adhesive. In each of these cases, by systematically controlling when bonding takes place, the bonding of a filament to any given surface or other object can be controlled.

In some exemplary embodiments, a printed filament can be stretched as it is deposited on, or at least towards, a surface or other object. More specifically, a nozzle can be positioned at a first location with respect to a surface or other object, and an initial portion of a filament can be deposited from the nozzle at a first site on the surface or other object. The nozzle can be moved to a second location with respect to the surface or other object, and while the nozzle is being moved, an additional portion of the filament can be deposited from the nozzle. Then the nozzle can be positioned at a third location with respect to the surface or other object, and an end portion of the filament can be deposited at another site on the surface or other object. This process can be repeated for an arbitrary number of points.

As part of inducing the stretching, the nozzle can be raised and/or accelerated as the nozzle moves to the second location, or any point subsequent to the first. Further, the deposited filament can be straightened by accelerating the nozzle at, near, or after the nozzle is positioned at the third location, or may point subsequent to the first. The amount of acceleration, which can also be zero or negative, can depend on many factors, including but not limited to the desired amount of stretching, the desired printing outcome, and other parameters that impact stretching of a filament, but in some exemplary embodiments, the acceleration that occurs as the nozzle(s) moves from the second to the third location (for instance by advancing and moving towards a surface) can be greater than the acceleration that occurs as the nozzle(s) moves from the first location to the second location (for instance by advancing and moving away from a surface).

The first and third locations can be proximate to the surface or other object to form anchors with the surface or other object at both ends of the filament, though any combination of locations can serve as anchors for printing filament. In some embodiments, the process can be repeated in substantially the same manner at different locations and positions (sometimes just slightly different locations and positions) to help form a three-dimensional object. Likewise, in some embodiments, multiple nozzles can be operated at the same time. A person skilled in the art, in view of the present disclosures, will understand how to print multiple filaments sequentially and/or simultaneously, and how to adapt various methods, systems, and devices provided for herein to accommodate multiplexing, i.e., the use of multiple nozzles at the same time.

A level of adhesion by any deposited filament to a surface and/or other object can be controlled using any number of techniques provides for herein or otherwise known to those skilled in the art. The level of adhesion can, for example, be controlled by the rate at which a solvent associated with the dope evaporates. As with the earlier described aspects, the rate at which the solvent evaporates can be controlled by adjusting a number of different parameters, including but not limited to a distance between a depositing end of a nozzle and a surface or other object onto which the dope is printed, a concentration of the solvent, and a rate at which the dope is deposited out of the nozzle. The dope, and thus ultimately the filament, can be deposited on any number of surfaces, including a flat surface, a contoured surface, previously deposited fluid/filament(s), etc. In some instances, the surface can be a three-dimensional template, to which the deposited filament can substantially conform, thereby taking the shape of the three-dimensional template. Further, the filament can include a wide variety of materials, including but not limited cellulose acetate, a thermoplastic, a thermoset plastic, nylon, polyester, and silk, alone or, in some instances, in combination. Still further, an antibiotic agent, electrically conductive additive, photocurable material, or any other functional additive can be included as part of any deposited material, and in some cases an interaction can then be initiated, to further enhance the properties and capabilities of the deposited material. This can be useful, for example, when the printed material is used in conjunction with an implantable medical device.

A person skilled in the art, in view of the present disclosures, will recognize how a system or device, such as a printer, can be made or otherwise adapted to control whether or not particular portions of a deposited filament bond to a surface or other object, as well as various features that can be included as part of the systems and devices to operate and/or enhance performance of the same. Components of a printer can include, but are not limited to, one or more drivers to advance one or more printheads on which one or more nozzles can be disposed, as well as a controller to control and/or operate, among other things, a print path along which the printhead(s) are moved and/or components of the printer that help control the rate at which a solvent associated with the dope disposed in the printer evaporates, or the rate at which a material loses its ability to adhere by another means (e.g., thermoplastics or thermosets).

In still some other aspects, the present disclosure provides for methods, systems, and devices that produce a three-dimensional printed object such as a fabric or a fabric-like part by creating a fully or partially-woven pattern, or a pattern that is not woven but bonded to create fabric-like mechanics. The present disclosure provides some non-limiting examples of paths (sometimes referred to as toolpaths) that nozzles can follow to produce the three-dimensional printed object. A person skilled in the art will recognize a variety of other paths that can be followed to create three-dimensional printed objects in view of the present disclosures without departing from the spirit of the present disclosure. By way of non-limiting example, although the embodiments illustrated in Appendix A illustrate the toolpaths as horizontal and vertical straight lines that are approximately 90 degrees with respect to each other, such illustration is only for purposes of easily describing representative, but non-limiting, embodiments. A person skilled in the art, in view of the present disclosures, will recognize many other configurations and paths that can be used. By way of non-limiting examples, one or more of the toolpaths illustrated as being parallel to each other can be angled with respect to each other, and one or more of the toolpaths illustrated as being perpendicular to each other can be at a non-right angle with respect to each other. By way of still further non-limiting examples, no toolpath needs to be straight from one end to the other. Each toolpath can have any number of twists, turns, contours, or other configurations. Likewise, any paths in the third-dimension (the z-direction or axis, i.e., into or out of the paper in at least some of the illustrated embodiments of Appendix A) can also take on any type of configuration, including being angled with respect to the x-direction or axis, y-direction or axis, and/or the x-y plane, and any toolpath in the z-direction can be straight, curved, twisted, etc.

In some exemplary embodiments, a three dimensional object is printed using a combination of warp and weft nozzles, such as a plurality of warp nozzles and one weft nozzle. As described herein, generally a warp nozzle can extrude filament that takes the place of warp filament in a traditional textile, while a weft nozzle can extrude filament that takes the place of weft filament in a traditional textile. A first subset of the warp nozzles can be advanced in a first direction while also ejecting a filament from one or more of the warp nozzles of the first subset. Subsequently, the weft nozzle can be advanced in a second direction. After that, a second subset of the warp nozzles, e.g., those warp nozzles that were not advanced as part of the first subset, can be advanced in the first direction while also ejecting a filament from one or more of the warp nozzles of the second subset. Subsequently, the weft nozzle can be advanced in the second direction, or alternatively, in a third direction that is opposite of the second direction with the second and third directions being approximately parallel with respect to each other.

In some embodiments, the second and third directions can be approximately perpendicular to the first direction, although, as described above, they do not necessarily have to be in such a configuration, nor do the first, second, and third directions have to be represented by straight lines. For example, an angle formed by the first and second directions can be approximately in the range of about 30 degrees to about 90 degrees, and in some embodiments the angle formed by the first and second directions is approximately 90 degrees. Regardless of the angles formed by any of the first, second, and third directions, the advancing of the first and second subsets of warp nozzles and the weft nozzle while also ejecting filament can be repeated one or more times until a desired three-dimensional printed object is formed. In fact, in some embodiments, the orientation of the paths, and which nozzles deposit filament during which passes along the paths, can change.

The weft nozzle can be advanced in the first direction without ejecting filament so that the weft nozzle can pass across different portions of filament ejected by the apparatus. In some embodiments, more than one weft nozzle can be used and/or weft or warp printheads can contain multiple weft and warp nozzles, respectively. Further, any of the ejected filaments can be stretched and/or straightened in a manner as described above or elsewhere herein, e.g., raising and/or accelerating nozzles and/or otherwise controlling a rate at which a solvent associated with an ejected dope or filament evaporates, or modulating filament length by any other method appropriate for that filament, as described herein or otherwise known by those skilled in the art in view of the present disclosure. The filament bonding can likewise be controlled by adjusting a number of different parameters, including but not limited to a distance between a depositing end of a nozzle and a surface or other object onto which the dope or filament is printed, a concentration of the solvent, and a rate at which the dope or filament is deposited out of the nozzle or any other method appropriate for that filament, as described herein or otherwise known by those skilled in the art in view of the present disclosure.

In some embodiments, the process can be repeated in substantially the same manner at different locations and positions (sometimes just slightly different locations and positions) to help form a three-dimensional object. Likewise, in some embodiments, multiple nozzles can be operated at the same time. A person skilled in the art, in view of the present disclosures, will understand how to print multiple filaments sequentially and/or simultaneously, and how to adapt various methods, systems, and devices provided for herein to accommodate such multiplexing.

The dope, and thus ultimately the filament, can be deposited on any number of surfaces, including a flat surface, a contoured surface, previously deposited dope/filament(s), etc. In some instances, the surface can be a three-dimensional template, to which the deposited filament can substantially conform, thereby taking the shape of the three-dimensional template. Further, the filament can include a wide variety of materials, including but not limited to cellulose acetate, a thermoplastic, thermoplastic polyurethane, polypropylene, a thermoset plastic, nylon, polyester, silk, elastomers, continuous fiber, semi-continuous fiber, and non-continuous pre-made fiber alone or, in some instances, in combination. Still further, an antibiotic agent, a photocurable material, an electrically conductive material, or any other functional material can be included as part of any deposited material, and then, at least in some cases, an interaction can be initiated to further enhance the properties and capabilities of the deposited material. This can be useful, for example, when the printed material is used in conjunction with an implantable medical device and/or a wearable sensor.

A person skilled in the art, in view of the present disclosures, will recognize how a system or device, such as a printer, can be made or otherwise adapted to print using warp and weft nozzles to print a three-dimensional object, as well as various features that can be included as part of the systems and devices to operate and/or enhance performance of the same.

Components of a printer can include, but are not limited to, one or more drivers to advance the warp and weft nozzles, as well as a controller to control and/or operate, among other things, the one or more drivers to selectively advance the nozzles as desired and/or components of the printers that help control the rate at which a material changes in its capacity to bond, for example how quickly solvent associated with the dope disposed in the printer evaporates, and/or how quickly a thermoplastic polymer cools, and/or how rapidly a thermoset polymer is heated.

Non-limiting examples of three-dimensional objects that can be printed using the methods, systems, and devices provided for herein include an article of clothing, an implantable medical device, and a wearable medical device. In view of the present disclosures, a produced three-dimensional object can be fully woven. Likewise, in view of the present disclosures, a produced three-dimensional printed object can be fully assembled without stitching, or with substantially less stitching than an object produced by methods not provided for in the present disclosure. In other words, once the system or device deposits filament, no further steps are needed to hold the printed filaments together because the system or device already sufficiently secured the filaments with respect to each other. Of course, other methods of bonding materials together, including but not limited to stitching, can be performed during or after the printing is completed; the present disclosure, however, is capable of significantly reducing and/or eliminating a need to do so.

In still further other aspects, the present disclosure provides for methods, systems, and devices that produce a three-dimensional printed object by printing across multiple layers, i.e., printing on multiple x-y planes during a single pass of a nozzle from one end of its path to another. In other words, an entire layer of a three-dimensional object is not necessarily completed before printing portions of another layer, each layer (i.e., each x-y plane) being at a different location along the z-axis. Furthermore, the difference in the z-height between each x-y plane may be less than the filament diameter, which can result in a partial mixing of layers.

In some such embodiments, filament can be deposited onto a surface or other objects from one or more warp nozzles as the nozzles make a first pass in an x-direction of a three-dimensional x-y-z coordinate plane, with the one or more warp nozzles moving in both the x-direction and a z-direction of the coordinate plane during the pass. Filament can be deposited during the pass, and, as a result, it can be deposited in multiple x-y planes. Likewise, filament can be deposited onto the surface or other objects from a weft nozzle as the nozzle makes a first pass in a y-direction of the coordinate plan, with the weft nozzle moving in both the y-direction and the z-direction of the coordinate plane during the pass. Filament can be deposited during the pass, and, as a result, it can be deposited in multiple x-y planes. Additional filament can be deposited by the one or more warp nozzles and/or the weft nozzle in a similar fashion such that the additional filament is also deposited in multiple x-y planes. As a result, multiple layers in the z-direction are printed simultaneously such that a single layer in an x-y plane of the multiple x-y planes remains incomplete while printing a portion of another layer in another x-y plane of the multiple x-y planes. It is also possible to make such parts with just a single muzzle moving in a similar manner instead of separate warp and weft nozzles.

The angles formed by the x, y, and z directions can vary. By way of non-limiting example, in one embodiment the x-direction can be any direction that forms an angle approximately in the range of about 45 degrees to about 90 degrees with respect to the y-direction in an x-y plane of the multiple x-y planes. By way of further non-limiting example, in one embodiment the y-direction can be any direction that forms an angle approximately in the range of about 45 degrees to about 90 degrees with respect to the x-direction in an x-y plane of the multiple x-y planes. By way of still a further non-limiting example, the z-direction can be any direction that forms an oblique angle with any x-y plane of the multiple x-y planes.

Any of the ejected filaments can be stretched and/or straightened in a manner as described above or elsewhere herein, e.g., raising and/or accelerating nozzles and/or controlling a rate at which a solvent associated with an ejected dope or filament evaporates. The latter can likewise be controlled by adjusting a number of different parameters, including but not limited to movement of the nozzle from which the filament is deposited in the z-direction, a solvent concentration associated with the deposited filament, and a rate at which the filament is deposited out of the nozzle.

The dope, and thus ultimately the filament, can be deposited on any number of surfaces, including a flat surface, a contoured surface, previously deposited dope, etc. In some instances, the surface can be a three-dimensional template, to which the deposited filament can substantially conform, thereby taking the shape of the three-dimensional template. Further, the filament can include a wide variety of materials, including but not limited to cellulose acetate, a thermoplastic, thermoplastic polyurethane, a thermoset plastic, nylon, polyester, silk, an elastomer, a continuous pre-made fiber, a semi-continuous pre-made fiber, and/or a non-continuous pre-made fiber, alone or, in some instances, in combination. Still further, an antibiotic agent, a photocurable material, an electrically conductive material, or any other functional material can be included as part of any deposited material, and then an interaction can be initiated, to further enhance the properties and capabilities of the deposited material. Such a combination can also include a pre-made continuous or semi-continuous filament, such as cotton, ballistic nylon, carbon fiber, cotton, nylon, polyester, rayon, cellulose acetate, polyurethane, an elastomer, polyester, silk, wool, or another fiber commonly used in textiles. This can be useful, for example, when the printed material is used in conjunction with an implantable medical device.

A person skilled in the art, in view of the present disclosures, will recognize how a system or device, such as a printer, can be made or otherwise adapted to print using warp and weft nozzles to print across multiple layers of x-y planes at the same time, as well as various features that can be included as part of the systems and devices to operate and/or enhance performance of the same. Components of a printer can include, but are not limited to, one or more drivers to move the warp and weft nozzles, as well as a controller to control and/or operate, among other things, the one or more drivers to selectively advance the nozzles as desired. The controller can also be used to control and/or operate parameters that impact stretching of filament as it is being deposited, e.g., raising and/or accelerating nozzles and/or adjusting one or more of a distance between an ejecting nozzle and a surface or object onto which the filament is ejected from the nozzle, a concentration of solvent associated with the filament to be printed by the nozzle, and a rate at which filament is deposited from the nozzle.

BRIEF DESCRIPTION OF DRAWINGS

This disclosure will be more fully understood from the following detailed description taken in conjunction with the accompanying drawings, in which.

DETAILED DESCRIPTION

Figure 1:
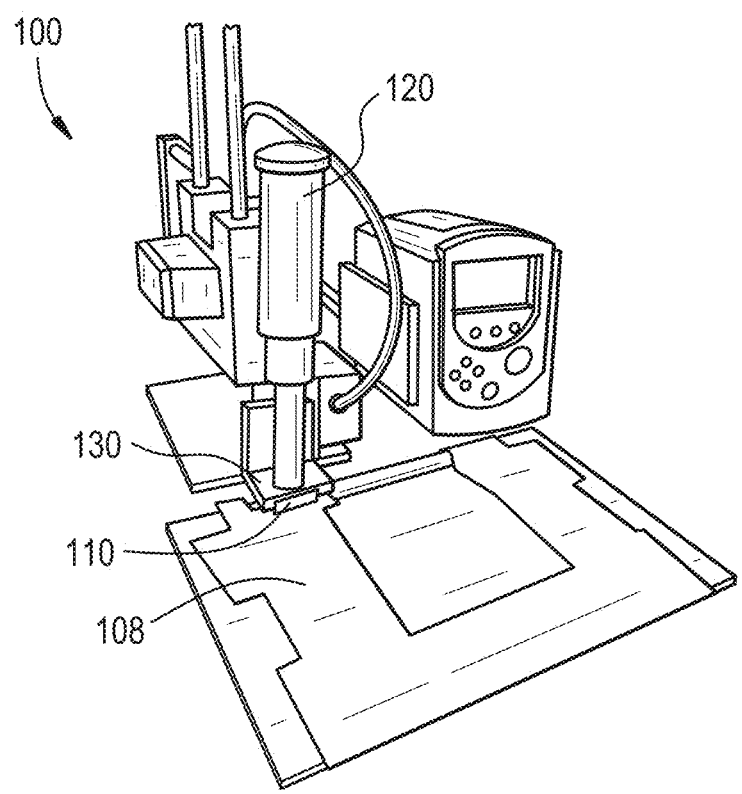
FIG. 1 is a perspective view of one exemplary embodiment of a 3D-printing device.

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent a term like "filament" is used herein a person skilled in the art, in view of the present disclosure, will understand that it includes a polymer extruded from a nozzle, a continuous, semi-continuous, or non-continuous pre-made fiber, or combinations thereof. As provided for herein, a filament can include a continuous, pre-made filament, an adhesive-coated filament, and an adhesive filament (i.e., where the material that the filament is composed of is itself made adhesive), among other filament configurations. Additionally, to the extent the terms "depositing" and "extruding" are described in the present disclosure, a person skilled in the art will recognize that "extruding" is one form of depositing a filament, and that it typically involves ejecting a material from a nozzle, while "depositing" more generally describes a variety of ways by which a material can be printed. While the present disclosure primarily describes depositing materials for printing via one or more nozzles, and thus primarily describes extruding, a person skilled in the art will recognize that the same techniques can be applied to other techniques for depositing materials during 3D printing, including powder bed sintering and stereolithographic methods. Accordingly, to the extent the term nozzle is used herein, a filament guide or other object used for depositing material can be used interchangeably or in conjunction with a nozzle.

The present disclosure generally relates to systems, devices, and methods for three-dimensional printing, and more particularly relates to deposition-based (e.g., extrusion-based) processes, systems, and devices to additively manufacture materials with controlled strength and flexibility, resulting in the ability to produce fabrics and other objects that are wearable and otherwise are conformable to a surface onto which they are placed. Each of the advances provided for herein, by themselves and in any combination, allows for the printing of materials such as fabrics, packaging, garments, clothing, medical textiles, medical implants, and wearable and/or implantable devices. The present disclosure highlights some of these advances with more particularity than others, although such highlighting by no means indicates the inventive nature of one advance or aspect in comparison to another. The present disclosure includes some illustrations and descriptions that include prototypes or bench models. A person skilled in the art will recognize how to rely upon the present disclosure to integrate the provided techniques, systems, and methods into a product, such as a consumer-ready, factory-ready, warehouse-ready, or lab-ready three-dimensional printer.

There are four aspects of the presently disclosed embodiments that are particularly useful in achieving 3D-printed objects (e.g., fabrics) that conform to surfaces: (1) the materials that are deposited during the printing process; (2) the ability to control inter-filament bonding between printed filaments; (3) toolpaths used to produce interwoven layers; and (4) the devices and systems that are used to produce fully woven fabrics. To that end, the resulting produced objects, which include but are not limited to fabrics, garments, and clothing, as well as medical components (e.g., medical textiles and medical implants) such as meshes, also represent significant developments in the field given the configuration of the produced objects in comparison to similar objects printed using more traditional methods. One key aspect to achieving objects of this nature is that the systems, devices, and methods provide for the local manipulation of the connectively between the material being deposited and the underlying support (e.g., the surface on which it is being printed, which may be an outside surface, or may be a previously deposited material(s)).

FIG. 1 provides one exemplary embodiment of a three-dimensional printing device or printer 100 set-up for printing in an x-y coordinate plane. The illustrated embodiment includes nozzles 110 and an air pump 120 for deposition of materials used in the printing process, but a person skilled in the art will recognize that various means of depositing materials onto a printing surface can be used. The materials deposited by the air pump 120 can include liquid inks that can be used to dissolve cellulose, cellulose acetate, as well as other materials. These materials can then be dissolved in a solvent that bonds as the solvent evaporates, thereby allowing rapid part production. The solvent used can be acetone, but a person skilled in the art will recognize that other solvents having rapid evaporation capabilities can also be used. Additional information about materials that can be used in conjunction with the printing devices, systems, and methods provided for in the present disclosure, including various deposition materials, solvents, adhesives, and materials to wash away materials that provided adhesive forces following deposition, are provided below, as well as throughout the present disclosure and those disclosures incorporated herewith.

In a bench model of the printer 100, the printer is a modified Printrbot Simple Metal, manufactured by Printrbot Inc. of Lincoln, Calif., where such modifications include replacing the standard printhead with the air-powered Nordson Ultimus I syringe pump, manufactured by Nordson Corporation of Westlake, Ohio. The air-powered syringe pump becomes a printhead 130 in this modified version of the 3D printer. However, many different 3D printers and air pumps, or similarly capable components, can be used in conjunction with the present disclosures. Components of a printer can include, but are not limited to, one or more drivers to advance one or more printheads on which one or more nozzles can be disposed, as well as a controller to control and/or operate, among other things, a print path along which the printhead(s) are moved and/or components of the printer that help control the rate at which a solvent associated with the dope disposed in the printer evaporates, or the rate at which a material loses its ability to adhere by another means (e.g., thermoplastics or thermosets). Various chambers for housing materials to be printed can also be part of the printer. The printer 100 is able to move across an x-y plane to deposit material onto a surface. The movement of the printer 100 in the x-y plane is a capability of 3D printers, and thus a description of how it is able to move in the x-y plane is unnecessary since it is understood by those skilled in the art.

The surface upon which the deposited materials can be printed can be any surface. In the illustrated embodiment, a surface 108 is substantially flat, and thus has its own x-y plane. However, in view of the present disclosures, the printer 100 can print onto a more contoured surface at least because the disclosures provided for herein allow the printed materials to conform to the surfaces onto which they are printed. Further, because 3D printing necessarily results in an object having three dimensions, and because the present disclosures relate to additive manufacturing, printing also occurs onto material that has already been deposited, such as filament or other materials previously deposited by the printer 100. In some embodiments, the surface onto which the material is deposited is an adhesive surface (i.e., a surface that is covered in an adhesive material).

As described in greater detail below, for instance when describing toolpaths and stretching a filament, a z-height of the printhead 130 can also be adjusted, thus allowing the printer 100 to print in three dimensions. A person skilled in the art understands how a 3D printer is able to move in a third plane to adjust a location of one or more nozzles 110 of the printhead 130, and thus further explanation is not provided herein. With that said, the actual process for how the printing is done, including but not limited to the toolpaths, the localized modulation of adhesion between printed materials, and stretching described below, are not disclosures that were generally within the art prior to the present disclosure.

Materials that can be used in conjunction with the devices and systems provided for in the present disclosure, like the printer 100, are vast, and can depend on a variety of factors, including but not limited to the desired properties of the object being printed (e.g., flexible and strong) and the desired use of the object being printed (e.g., a mesh for use in a soft tissue repair, such as a hernia). The present disclosures allow the materials being used to form a fabric that includes robust, locally defined mechanics that can be tailored to fit any surface.

In some exemplary embodiments, cellulose and cellulose acetate can be used for structural materials and 3D printing. The cellulose molecule can be a linear polymer with a repeating unit consisting of two anhydroglucose rings. $(C_6H_{10}O_5)n$ where n=10000 to 15000, that can be linked by covalent bonds. Cellulose can a preferred material because it is the primary reinforcement phase of many biological organisms, including trees, plants, algae, some sea creatures, and bacteria, and is also the most abundant organic polymer on Earth.

One having ordinary skill in the art will appreciate that in some embodiments, cellulose acetate, which is a functionalized form of cellulose, can be used instead of cellulose. Both cellulose and cellulose acetate are biocompatible, biodegradable, pleasant to the touch and inexpensive, making them excellent choices for mass manufacture of wearables and implantable devices. Both molecules are also compostable, dry quickly, are shrink, mildew, and moth resistant, are washable or dry cleanable, and are easily dyed.

Cellulose acetate differs from cellulose in that approximately ⅔ of the hydroxyl groups on the cellulose molecule have been replaced by acetate groups. While this can reduce the number of hydrogen bonds in the material and thus its tensile strength, the cellulose acetate can become soluble in acetone, which enables the 3D printing process described herein. Additionally, for applications in filtration or microfluidics, cellulose acetate is also hydrophilic, has high surface area, and absorbs organics, allowing it to be used to produce specially structured separation membranes or even implantable sensors/filtration devices. It is also strongly dielectric and can be used to produce actuators in prostheses, as well as in robotics or haptic interfaces.

In some exemplary embodiments, cellulose acetate, after printing, can also be converted into pure cellulose for structural materials and 3D printing by treating the cellulose acetate in sodium hydroxide. Use of pure cellulose can enable the manufacture of parts with exceptional mechanical properties, or conversion into other cellulose derivatives such as rapidly biodegradable methylcellulose. Cellulose is also a very versatile material in that it is easily functionalized into forms with other useful properties such as methylcellulose and carboxymethyl cellulose, both of which are water soluble and rapidly biodegradable. In addition to its low cost and environmental benefits, cellulose can have specific tensile strength and stiffness in its crystalline form of 4.75 GPa cm$^3$/g and up to 138 GPa cm$^3$/g, respectively.

Converting 3D printed cellulose acetate parts into pure cellulose enables the 3D printing of exceptionally strong but flexible materials that are also much more mobile than cellulose to allow the molecules to more easily align. The flexibility of the cellulose acetate filaments to selectively slide over each other can also enable production of flexible and conformable parts. For example, pure cellulose has an axial tensile strength of ~25 MPa and an inter-filament tensile strength of ~13 MPa, which is comparable to other polymers such as nylon, polyester, and silk that are used in textiles. Highly aligned pure cellulose can be used where high tensile strength is required, for example in hernia repair, while methylcellulose can be used for applications where relatively rapid biodegradation in the body is desired. The resultant textiles can also locally be coated with drugs or cell-growth medium to further improve their interface with the body and their therapeutic value. In some embodiments, materials such as thermoplastics (e.g., Nylon or polypropylene), thermosets, or polymers can be used to additively manufacture fabrics using the extrusion-based processes described below. One or more of these materials can be used in combination on a per-filament or per-object basis. For example, different materials can be used to produce different rates of biodegradation, and thus mechanical compliance with time spent implanted, for a medical implant.

In accordance with the present disclosures, adhesives can be used both to pattern filament, for example when moving a pre-made filament over an adhesive surface to draw the filament out of the nozzle, and to modulate the structure and mechanics of meshes, for example by bonding pre-made filament at different positions to give a mesh a desired geometry and mechanical response. If an adhesive is used to help manufacture a mesh, but is not required or wanted in the eventual mesh, then the adhesive can be washed off during or after the manufacturing process. In a typical case, a surface covered in water soluble adhesive can be used to draw pre-made filament out of a nozzle, and once all of the filament has been deposited and the permanent adhesive (that which is intended to be a permanent part of the mesh) has also been deposited onto the mesh, the mesh can be washed in water to remove the unwanted adhesive. Permanent adhesive is typically used to bond pieces of pre-made fiber to give a mesh cohesion and to modulate its geometry and mechanics. The use of permanent adhesive thus allows the manufacture of a desired shape from fibers that would otherwise not bond to one another (such as Kevlar or carbon fiber).

A number of different techniques can be used to incorporate permanent adhesive as part of the eventual end product (e.g., a mesh, garment, etc.). In some instances, a pre-made filament can be deposited in a desired pattern as described herein or as otherwise derivable from the present disclosures and then adhesive can be deposited onto the patterned filament. The adhesive can also be used after filament patterning to further modulate printed object (e.g., mesh) mechanics and geometry, for example by providing an elastic bridge between two pieces of filament, or surrounding a filament to increase its effective diameter, and thus stiffness. Adhesive can also be added at other times of the printing process, depending, at least in part, on the eventual desired structure and composition of the printed object and the desired bonding techniques to be used during printing. For example, to insure adhesive coverage over an entire diameter of filament, it may be helpful to pattern adhesive onto a surface before the filament is deposited. It may be further helpful to deposit adhesive after the filament is deposited as well. This can help insure that the underside of the filament is also covered with adhesive as desired. Similarly, filament may be immersed in photopolymer and light shone on the regions to be bonded to pattern the adhesive. A person skilled in the art will recognize other ways by which adhesive can be associated with filament without departing from the spirit of the present disclosure in view of the other disclosures provided for herein.

In an exemplary embodiment of an extrusion-based printing process, a polymer, such as cellulose acetate, can be dissolved in a solvent to make a viscous fluid, sometimes referred to as dope. The viscous fluid can then be ejected from the printer 100 through the nozzle 110 in the printhead 130 to form a filament that is deposited in a series of layers for additive manufacturing.

One having ordinary skill in the art will appreciate that a filament guide can be used interchangeably or in conjunction with the nozzle, and that the printer 100 can include multiple nozzles that are configured to deposit filament onto a surface. In the illustrated embodiment of the printer of FIG. 1, the nozzles can have diameters of approximately 200 μm at their distal tips, though it will be appreciated by one skilled in the art that the diameter of the nozzles can vary. The nozzles can extrude filament of different diameters, such as approximately 50 μm, approximately 100 μm, approximately 200 μm, and so forth. Filament having larger diameters, such as filaments greater than 200 μm, can reduce the surface area of the mesh, which can reduce the reaction from host tissue. Filaments can also have any size length, depending, at least in part, on the desired size of the object being printed. In one exemplary embodiment, a diameter of a filament is at least about 1 μm and a length of a filament is at least 10 mm, and in another exemplary embodiment, a diameter of a filament is at least about 100 μm and a length of a filament is at least 100 mm. The viscous fluid can be highly adhesive when acetone is present, but the viscous fluid can bond and harden rapidly as the acetone evaporates. The solution is highly shear thinning, and the rapid evaporation of the solvent further increases the viscosity of the viscous fluid after ejection, which results in excellent dimensional control of printed parts.

The systems, devices, and methods disclosed herein can allow a user to control whether the filament bonds to the previously deposited layer at any given point or allows the layers to slide over each other to make them highly flexible. Control of interfilament bonding and interlayer adhesion, referred to herein as modulating adhesion or referenced using other similar terms, can restrict the layers' ability to conform to surfaces and can be achieved by changing whether the solvent has evaporated when the extruded filament comes into contact with the previous layer. Parameters such as printhead z-height, solvent concentration, and viscous fluid extrusion rate can be changed to influence bonding and adhesion. In some embodiments, the printhead can be relatively close to the surface, which can cause the viscous fluid to be adhesive when it reaches the surface and adhere to the underlying layer. In some embodiments, the printhead can be positioned at a distance from the surface, such that the solvent is largely evaporated by the time the filament reaches the substrate, thus preventing filament bonding. For example, filaments that are extruded from a 200 μm diameter nozzle have been shown to no longer be adhesive after ~0.5 s at 35 wt. % cellulose acetate in acetone. The lack of bonding allows stretching the filament as it is deposited, which improves molecular alignment and significantly enhances tensile strength. Initially, when the viscous fluid is extruded, the extrudate has a relatively high surface area:volume ratio. Higher surface area:volume ratios allow acetone to evaporate more rapidly, which causes rapid hardening of the polymer. Using solvent evaporation as a means of hardening the material enables very rapid manufacturing by sidestepping the primary rate limitation of FDM processes of rapid filament heating without damage.

Further, many pieces of filament can be deposited simultaneously. The process outlined herein is very economical because it is rapid and carried out under ambient conditions with a simple air compressor required for extrusion. Moreover, polymers such as cellulose and cellulose acetate are highly abundant while the evaporated acetone is both inexpensive and can be recycled. Additionally, each item is produced as a single part, largely removing the need for assembly and therefore enabling full automation of the production process. Also, it will be appreciated by one skilled in the art that the methods disclosed herein provide for massive parallelization of textile manufacture through the use of multiple printheads.

Figure 2:
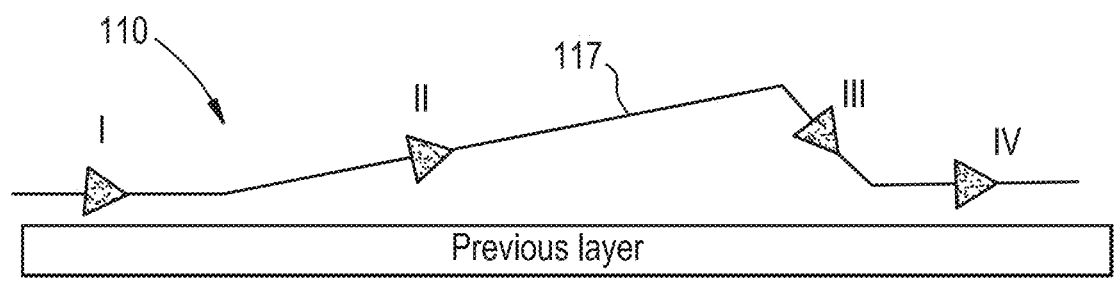
FIG. 2 is a schematic illustration of one exemplary embodiment of a tool path for use in conjunction with 3D-printing methods provided for herein.

FIG. 2 illustrates a sample toolpath for direct write deposition of a filament material from a nozzle 110 to produce non-bonded layers of filament. Filament, as described herein, can be both a continuous length of material that is passed through a nozzle, but is not shaped by the nozzle (e.g., a pre-made rope), as well as material that is actively shaped by the nozzle into a filamentary form (e.g., molten plastic that is extruded through the nozzle). When a filament is pre-made, continuous length, it can also be described as a fiber or a pre-made filament. With respect to an entire printed object or part, a continuous filament or fiber may be an entire length of the object or part such that a length of the filament or fiber is the length of the object or part.

As shown at (I) of FIG. 2, in preparation for depositing filament, the nozzle 110 can travel close to a substrate or previously printed part to anchor the filament. To control interlayer adhesion and bonding, the nozzle 110 can lift off the substrate as it extrudes filament, while accelerating in a printing direction, as shown at (II) of FIG. 2. Locally manipulating the connectivity between the material being deposited and the underlying support by having the filament jump over an orthogonal fiber crossing enables the extruded material to solidify or cure without adhering to the underlying fiber. This, in turn provides the fibers with the freedom to slip in the fabric, whereas not jumping causes the fibers to adhere, resulting in higher local stiffness of the filament.

The ability to control whether interlayer bonding takes place, i.e., modulating adhesion, represents a unique opportunity to control part rigidity through its topology, and therefore to make parts that are more flexible and conformable than is possible with homogenously bonded structures. Adhesion can be modulated on a filament-by-filament basis (i.e., it can be modulated while an individual filament is being deposited), as well as on a layer-by-layer basis (i.e., it can be modulated while one layer of a plurality of filaments is being deposited on a previous layer of a plurality of filaments), during 3D printing. Further post-processing of a printed filament(s), for example hydrolysis in sodium hydroxide, can significantly further improve the mechanics of the resulting object. The method of controlling interlayer bonding is not limited to solvent-based deposition systems. In some embodiments, the same principle can be applied to 3D printing methods where bonding in the part is controlled by other substances such as thermoplastic polymers, thermoset polymers, photopolymers, or mixtures thereof. For example, to control bonding of a thermoplastic polymer printed by extrusion, the heated printhead can be lifted up and accelerated to prevent bonding, then brought down again to bring the filament into contact with the previous layer to induce bonding. Similarly, for extrusion of a thermoset polymer, as in some embodiments, the interlayer bonding can be controlled by providing heat to the polymer by selectively bringing it into contact with previous layers at temperature at the points where bonding is desired, for example through a heated nozzle or through a laser.

In view of the present disclosures, a non-exhaustive list of the way by which modulating adhesion of filaments can occur includes: (1) bringing the filament into contact with the at least one of the surface and the one or more previously deposited filaments; (2) controlling a rate at which a solvent associated with the filament evaporates prior to the filament coming into contact with at least one of the surface and the one or more previously deposited filaments; (3) selectively exposing regions before, during, or after depositing the filament to light able to cure a photopolymer, or a material having light-responsive bonding agents associated therewith; (4) selectively exposing regions to heat before, during, or after depositing the filament; (5) selectively using an adhesive at regions before, during, or after depositing the filament; and (6) selectively using an adhesive to provide bonding between the filament and the one or more previously deposited filaments. Any adhesion modulation technique provided for herein can be used independently, and a person skilled in the art will recognize that some or even all of the techniques can be used in conjunction with each other, depending on various factors, including but not limited to the type of object being printed, the components of the printer, and the preferred techniques of the operator of the printer. Further, as described in greater detail below, by modulating adhesion, it allows various properties of the resulting object (e.g., fabric) to be controlled, the properties including deformation, electrical conductivity, thermal conductivity, and toughness, among others.

As further shown at (III) of FIG. 2, the nozzle 110 can move back towards the surface of the substrate to complete the extrusion process. As shown, the location of the nozzle 110 at (I) and (III) is proximate to the surface. It will be appreciated by one skilled in the art that the nozzle 110 can continue to be accelerated to further straighten the non-bonded filament. Once the nozzle 110 returns approximately to its original height or contacts the substrate, the nozzle 110 can anchor the filament to the substrate, as shown at (IV) in FIG. 2. In some embodiments, the "anchoring" areas that occur in steps (I) and (IV) to provide adhesion that allow the stretching of the filament are sometimes larger than would be wanted in the final part. In this case, some of the anchoring regions can be removed after printing has occurred in multiple ways, such as by cutting the anchors with a blade.

The amount of acceleration during the process, which can also be zero or negative, can depend on many factors, including but not limited to the desired amount of stretching, the desired printing outcome, and other parameters that impact stretching of a filament, but in some exemplary embodiments, the acceleration that occurs as the nozzle(s) moves from the second to the third location (for instance by advancing and moving towards a surface) can be greater than the acceleration that occurs as the nozzle(s) moves from the first location to the second location (for instance by advancing and moving away from a surface).

Figure 3A:
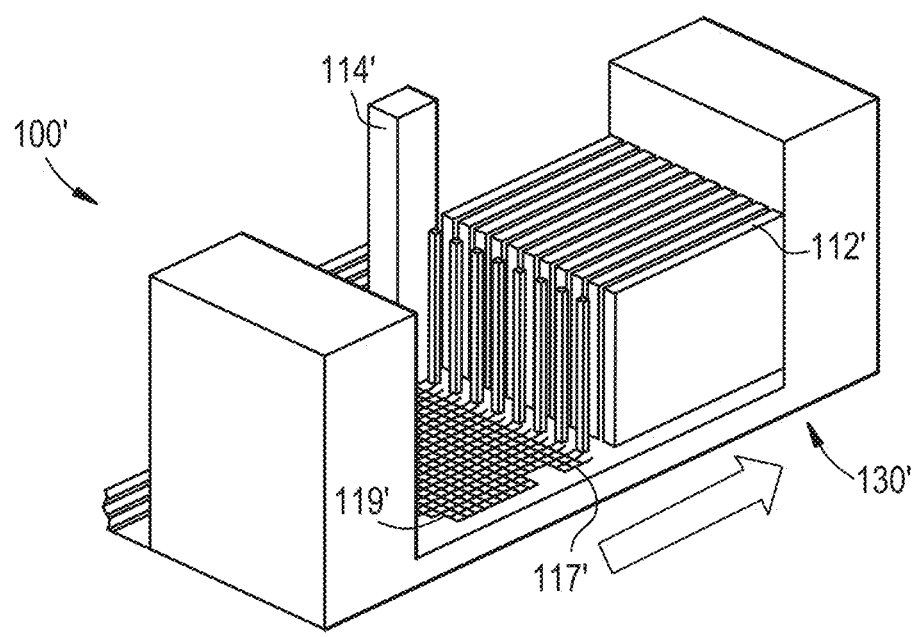
FIG. 3A is a schematic perspective view of another exemplary embodiment of a 3D-printing device.
Figure 3B:
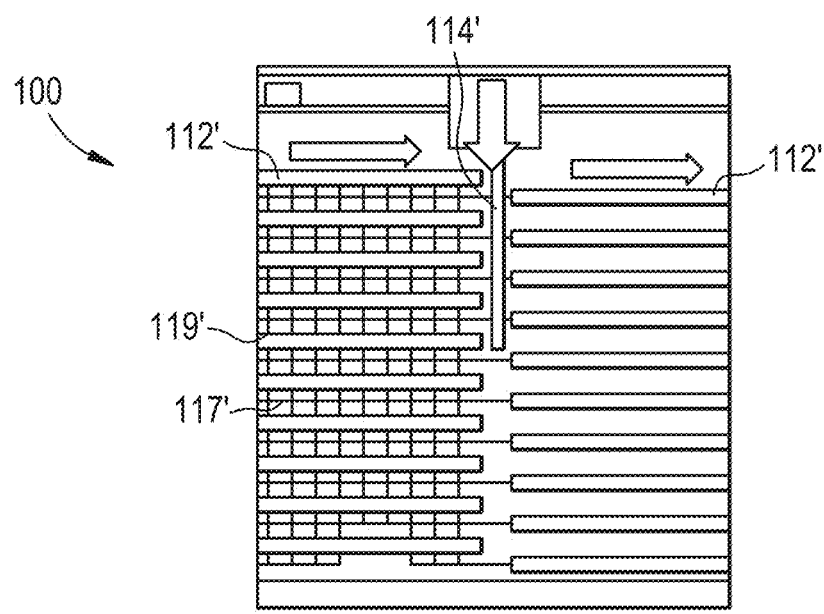
FIG. 3B is a schematic top view of the 3D-printing device of FIG. 3A.

Once extruded, the non-bonded filament can be patterned into fabrics. FIGS. 3A-3B illustrate the schematics of an embodiment of a 3D printer 100' design for producing fully woven fabrics using the toolpath described above, in which the arrow indicates the direction of printing. The printer 100' can include a printhead 130' having one or more nozzles 110' for depositing filament onto a substrate or onto another surface, similar to a configuration described above. By depositing the material on a template surface, for example one made by 3D printing, non-planar fabrics that are exactly fitted to the template surface can be produced. Additionally, the configuration of the nozzles can control the location where filament can be deposited, which allows for unprecedented customization at a high manufacturing rate and low cost because garments without any stitching assembly required can be produced.

As shown, the printer 100' includes warp nozzles 112' and weft nozzles 114'. For ease of illustration, the embodiment provided only includes a single weft nozzle 114', although the present disclosure generally provides for multiple warp and weft nozzles. With that said, embodiments including only a single warp or weft nozzle are still within the spirit of the present disclosure. In fact, it will be appreciated by one skilled in the art that any number of warp and weft nozzles can be used without departing from the spirit of the present disclosure. In an exemplary embodiment, the weft nozzle 114' can be positioned to travel substantially perpendicularly to, and in between, the warp nozzles 112'. As described in greater detail with respect to FIGS. 4A-4F, this configuration allows filament deposited from a one of a weft and warp nozzle to be deposited both above and below a single filament deposited from the other of the weft and warp nozzle, creating a woven configuration. It will be appreciated by one skilled in the art that the nozzles can have varying angles, e.g., parallel, acute, obtuse, and so forth, and travel in varying directions relative to one another.

The warp nozzles 112' can each deposit filament, and thus for ease of description, filament deposited from a warp nozzle 112' is described as a warp filament 117' herein, and filament deposited from a weft nozzle 114' is described as a weft filament 119' herein. It will be appreciated by one skilled in the art, however, that each nozzle can contain varying substances that can be used to produce a fully woven fabric since the present disclosure is not limited to the deposition of filament.

Figure 4A:
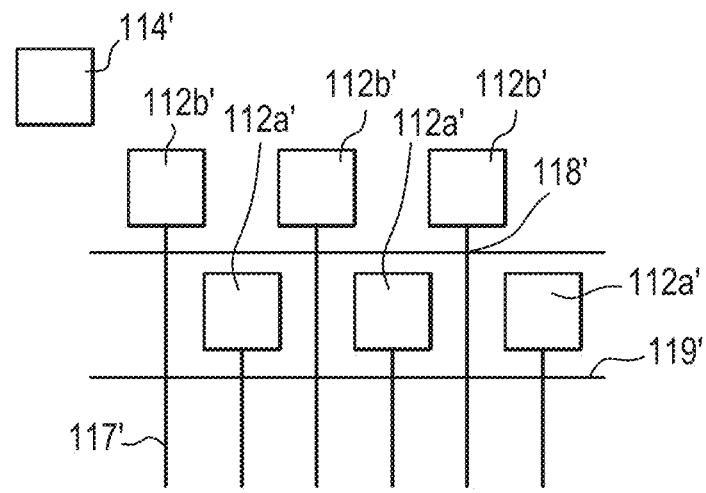
FIGS. 4A-4F is a schematic illustration of one exemplary embodiment of a printing method involving a plurality of nozzles, with each figure providing for a different stage in the method as nozzles of the plurality of nozzles move with respect to a surface onto which printing occurs.

FIGS. 4A-4F illustrate a time-lapse schematic of one embodiment of the nozzles 112', 114' of the printer 100' as they produce fully woven fabric. Filament is deposited in a grid-like pattern such that a single volume of filament passes alternatively over and then under adjacent rows of filament to form a fully woven fabric. As shown in FIG. 4A, two sets of three warp nozzles 112a', 112b' and a single weft nozzle 114' are pictured, though again it will be appreciated by one skilled in the art that various configurations and amounts of nozzles can be used without departing from the spirit of the present disclosure.

Figure 4B:
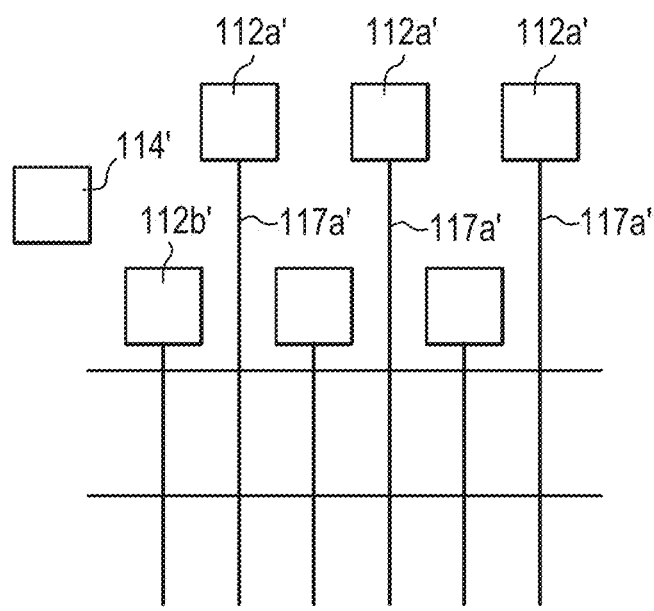
Figure 4C:
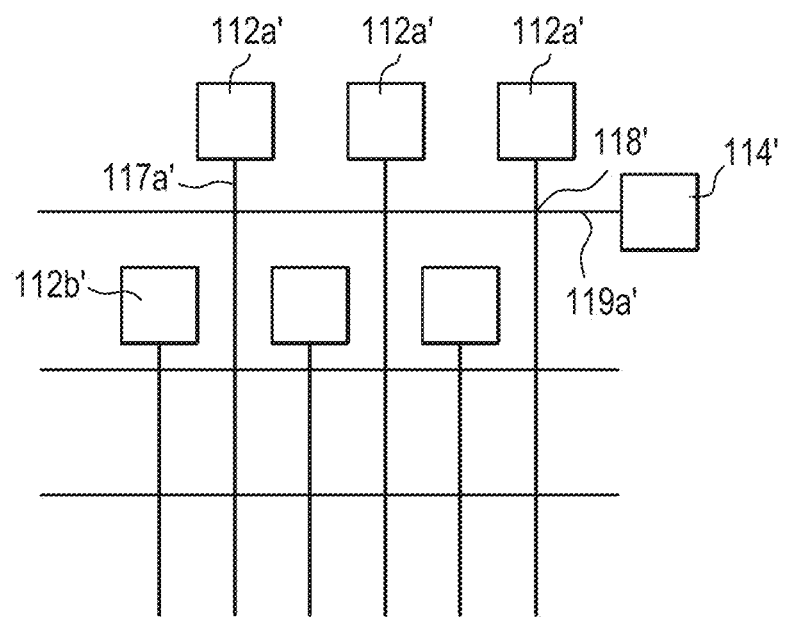

As shown in FIG. 4B, one set of warp nozzles 112a' advances, depositing warp filament 117a' as the nozzles advance. The weft nozzle 114' is then advanced, which can deposit weft filament 119a' over the warp filament 117a', as shown in FIG. 4C. Bonding between the warp filament 117a' and the weft filament 119a' can occur at the nodes 118', which are the intersections of the filaments. The filaments can be bonded or not bonded at every node. One having ordinary skill in the art will appreciate that the distance between each node can be configured according to user inputs to the printer 100', which can thus vary these distances. Appropriate patterning of bonded and non-bonded nodes can give excellent mechanical control and fabric-like mechanics regardless of the presence of filament interweaving. The nodes can bond by different means, which can result in varying mechanical responses in terms of strength and elasticity. Different means of inducing bonding at nodes includes but is not limited to: solvent-based, photopolymerization, thermoplastic, thermoset, or friction through interweaving. The bonding between the filaments at nodes can also take on different forms that allow for mechanical variation. For example, a part can include a strong fiber and an adhesive, and/or elastic fiber to provide tough bonding between strong fibers. In other embodiments, adhesive can be deposited across different fabrics or within a single fabric.

Figure 4D:
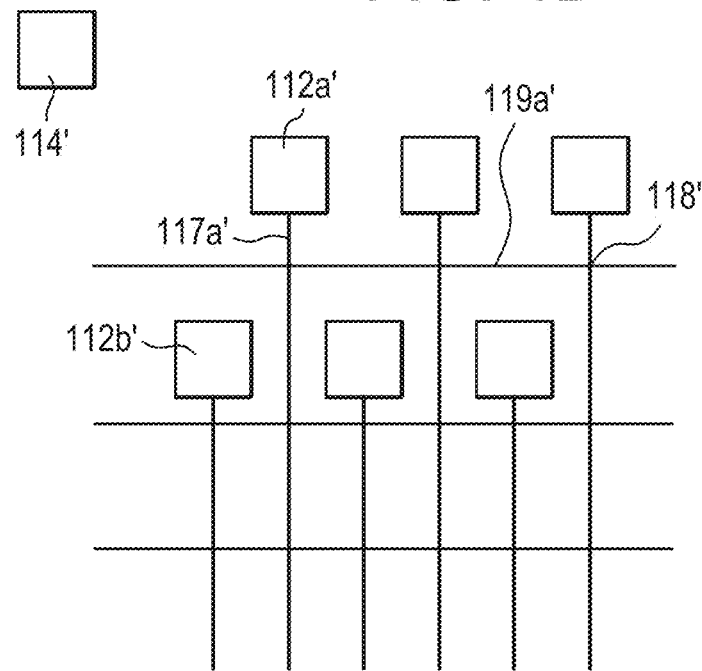
Figure 4E:
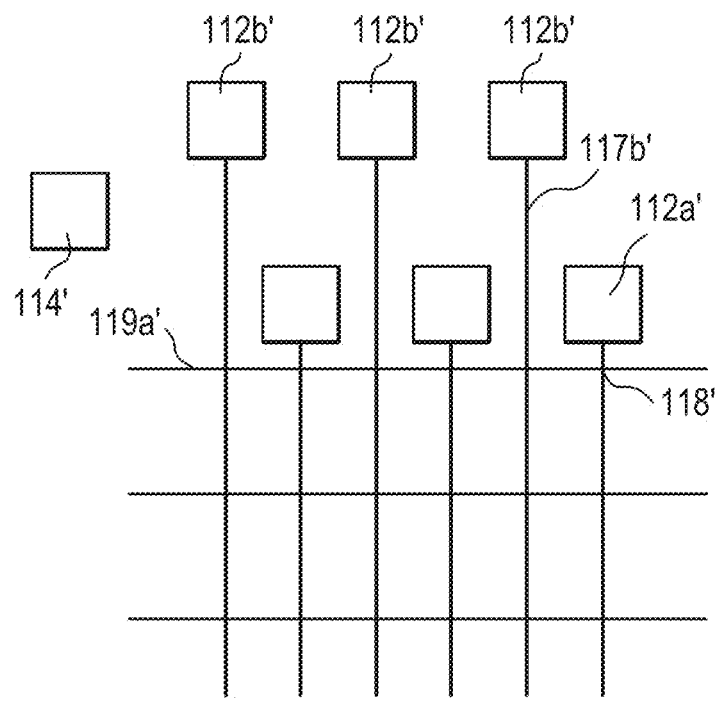
Figure 4F:
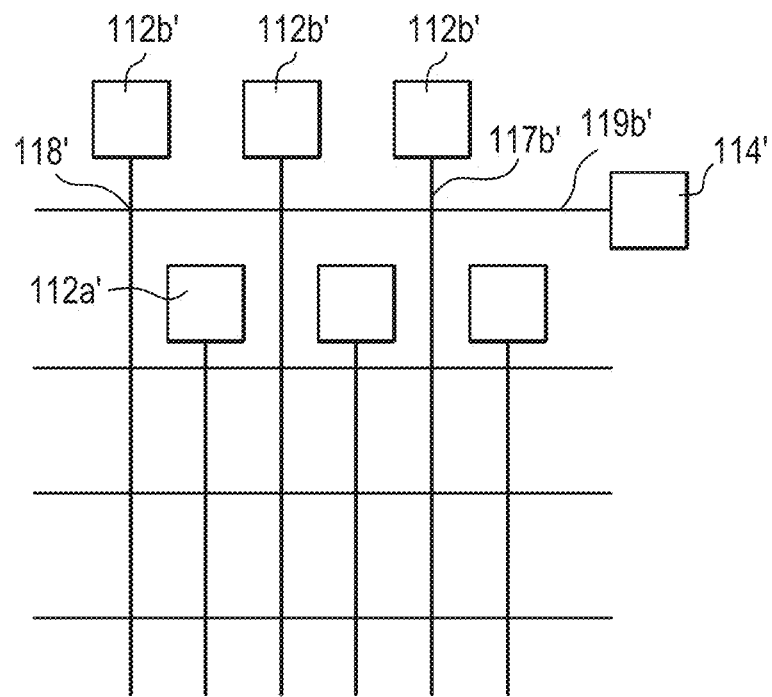

After depositing the filament, the weft nozzle 114' can retract, as shown in FIG. 4D. Once retracted, the second set of warp nozzles 112b' can advanced. The warp nozzles 112b' deposit warp filament 117b' over the weft filament 119a', as shown in FIG. 4E. The weft nozzle 114' can then advance over the just deposited warp filament 117b' to deposit weft filament 119b', as shown in FIG. 4F. Alternating warp filament 117a', 117b' and weft filament 119a', 119b' in such a pattern can provide the non-bonded regions of the part with mechanical stability despite their extreme flexibility. It will be appreciated by one skilled in the art that the interlayer bonding of a part can be distributed such that desired mechanics are achieved. Because the vertical motion and rate of filament deposition of each nozzle can be controlled individually, this method of printing enables the production of non-planar and arbitrarily shaped fabrics, enabling the full production of garments as a single piece and with no assembly required.

It will be appreciated by one skilled in the art that various weaving arrangements are possible, which can alter the sequences of motion of the nozzles and deposition of filament. For example, filament can be deposited so as to interweave different layers of filament in a grid-like pattern, though it will be appreciated by one skilled in the art that filament can be distributed in an arbitrary pattern or to produce analogues of any symmetrical weave, including plain weave and basketweave, that are used in many woven fabric applications such as apparel and composites.

A particular advantage of this method of printing fabrics that should be noted is that, while conventional textile production machines only produce planar fabrics, that are then cut out into standardized shapes, the disclosed process enables the printing of fabrics onto templates that can be shaped to produce a fabric that conforms to any desired surface. The length and position of each of the fibers in the part take on a length that allows coverage of complex surfaces by printing on the template, the template having a shape that is designed to produce a part able to conform to a given surface. Notably, the template does not need to replicate the surface that the printed part is meant to cover because the part is flexible. Printing the part in one configuration, whether on a template, or on another surface, may be easier than printing it in the exact configuration in which it is to be worn.

It will be appreciated by one having ordinary skill in the art that the bonding principles described herein can also be applied to material systems that include continuous, semi-continuous, or non-continuous pre-made fibers. These include carbon fiber, cotton, nylon, glass, polyester and other fibers commonly used for purposes including, but not limited to, mechanical reinforcement, garment production, electrical or thermal conductivity, or other functionalities. Thus, for example, a pre-made fiber could be patterned in the same way as an extruded filament, but with the difference that another material is used to provide the adhesion that other filaments are able to produce on their own through their respective bonding mechanisms. e.g., solvation for dissolved polymers. Further, the modulation of material and adhesion can be used to control properties of junctions, for example conductivity and pressure sensitivity, and to produce parts/fabrics with spatially controlled electrical response.

Rather than simply changing the outline of the fabric, the systems, devices, and methods disclosed herein are capable of controlling the length, orientation, bonding, conformation, and placement of every individual filament that forms the printed fabric. This enables the complete customization of the fabric to the surface and forces it will experience.

These methods also can be used to produce garments or medical textiles that are distinct and cannot be made in any other way by producing a non-woven fabric where filament is selectively bonded, instead of or in combination with being interwoven. Filament can be selectively bonded at junctions at which they intersect, or along longer lengths or bigger areas, which can be accomplished, for example, by using an elastic adhesive. The fabric is considered non-woven because each filament or fiber layer is layered on top of another filament and fabrics do not pass over and under adjacent pieces of filament in the way that is characteristic of woven fabrics. The distribution of bonding sites in these garments differs from bonding in traditional nonwoven fabrics in that in traditional nonwovens the distribution is random, because it is caused by large area techniques such as rollers that cannot place discrete bonds at any particular site. The placement of each bonding site is discrete and/or rational, and deliberate. Additionally, the elasticity or other mechanics of a part of the instantly disclosed meshes and fabrics produced by these methods can also be tuned by changing the length of diameter of filament in any given section. For example, in an exemplary embodiment, a filament may be lengthened in a particular section such that when it is not pulled, it is partially or fully folded, but when pulled it straightens and eventually becomes taut, which can allow the material to expand. Similarly, in some embodiments, instead of there simply being a direct bond between two pieces of filament at a node, another piece of filament or elastic adhesive can be deposited in between the two pieces of filament forming the node to modulate the mechanics of the node, for example by increasing its elasticity. In some embodiments, instead of being placed in a nozzle, the filament can also be gripped at its end and lowered onto a template, thereby conforming to the surface. The template can be covered in adhesive to keep the filament in place, or adhesive can be deposited onto the filament. In other embodiments, multiple pieces of filament can also be lowered onto the surface in parallel.

Figure 5A:
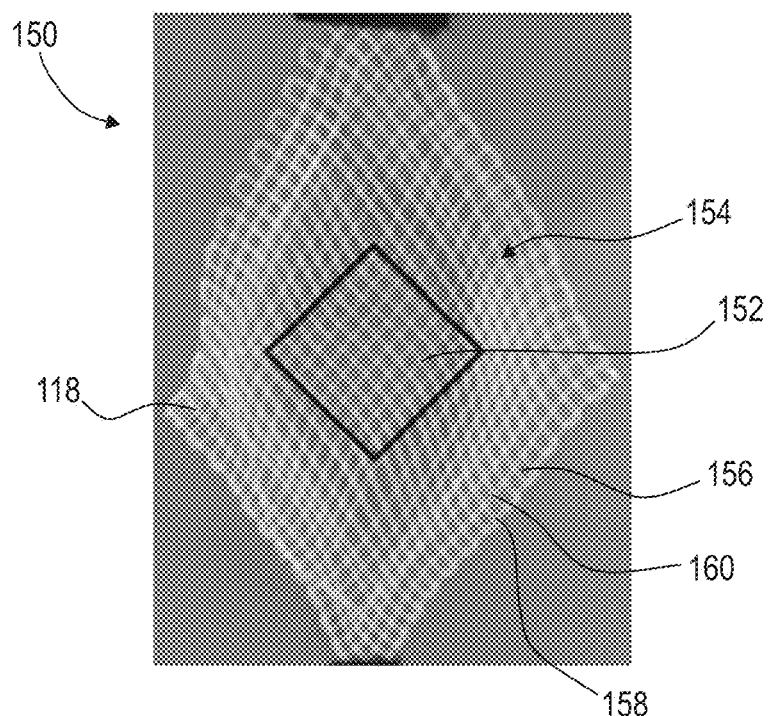
FIG. 5A is a top view of one exemplary embodiment of a mesh produced using an exemplary printing technique provided for herein, the mesh having a central region that includes bonded nodes and a periphery portion that does not included bonded nodes.
Figure 5B:
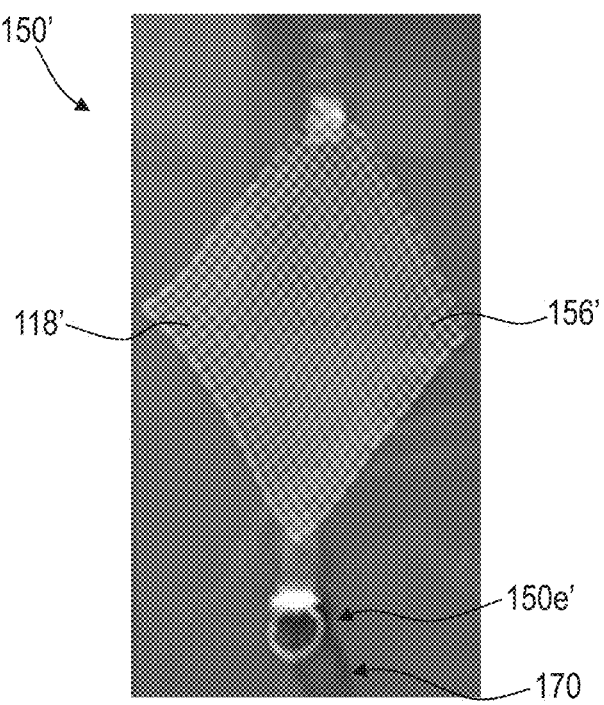
FIG. 5B is a top view of another exemplary embodiment of a mesh produced using an exemplary printing technique provided for herein, the mesh having all interlayer nodes bonded, and a weighted component being associated with the mesh.
Figure 5C:
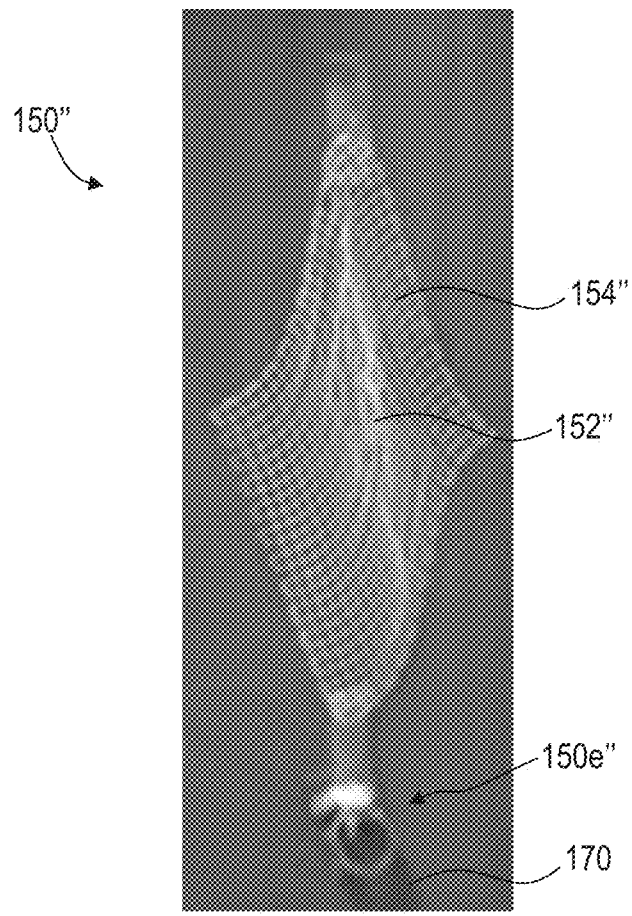
FIG. 5C is a top view mesh having similar characteristics as the mesh of FIG. 5B except rather than having all interlayer nodes bonded, nodes in a central region are not bonded, the mesh having the weighted component of FIG. 5B associated therewith.
Figure 5D:
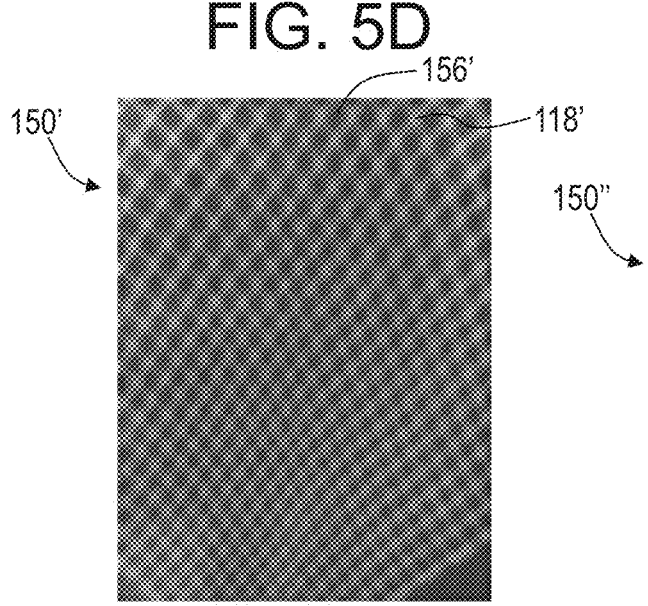
FIG. 5D is a detailed top view of a central region of the mesh of FIG. 5B.
Figure 5E:
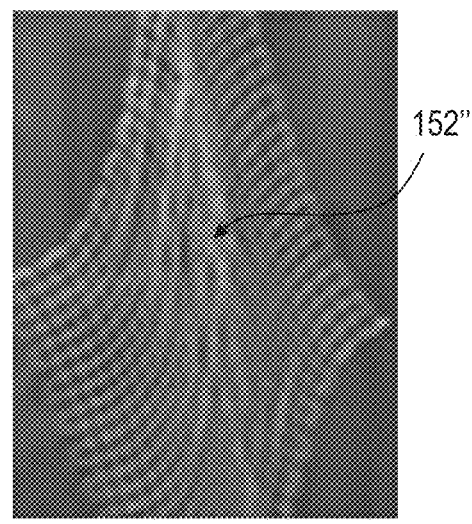
FIG. 5E is a detailed top view of the central region of the mesh of FIG. 5C.

FIGS. 5A, 5B, and 5C respectively illustrate examples of a mesh 150, 150', and 150" that can be manufactured via the methods described herein. FIG. 5A provides for a mesh 150 having a central portion 152 that includes bonded nodes, FIG. 5B, provides for a mesh 150' in which all interlayer nodes are bonded, and FIG. 5C provides for a mesh 150" in which a central portion 152" does not have bonded nodes. In general, meshes provided for in the present disclosure can have a uniform pattern and bonding of filaments throughout, or alternatively, they can include local variations. Local variations allow different portions of the mesh across its surface area to have different properties, i.e., it can be stronger and/or more flexible at some locations than others. The ability to locally vary the properties of the mesh, and in particular to locally vary them for every iteration of the product (i.e., individual customization) is another unique feature of this process.

In the illustrated embodiment of FIG. 5A, the mesh 150 includes a local variation, as the marked central portion 152 of the mesh 150 includes bonded nodes, while the remainder of the mesh, i.e. a peripheral region 154, does not. The nodes 118 are the location of intersection between the filaments. Characteristics of the mesh, such as pore size, can be varied to customize the fit of the mesh. In the illustrated embodiment, the pores 156 are each of the spaces disposed between the crossed filaments 158, 160 of the mesh 150. Smaller pores can cause the central portion 152 to have a greater stiffness than the remainder of the mesh, which can be a useful feature in preventing a hernia from deforming the mesh and thus recurring, while larger pores can be used in portions that require closer integration with tissues. The remainder of the mesh is configured to maintain its flexibility due to non-bonded nodes, which can minimize discomfort when worn post-surgery. One having ordinary skill in the art will appreciate that the size of the central portion of the mesh having bonded nodes can vary. The mesh can also be manufactured such that the central portion includes non-bonded nodes while the remainder of the mesh includes bonded nodes.

Prior to the present disclosure, small gaps were typically found at the nodes of crossing filaments. These gaps are referred to by those skilled in the art as interstices. The printing techniques provided for herein, such as the selective localized node bonding, allows the resulting fabric to be devoid of interstices between the filaments that are bonded together. This is because, prior to the present disclosure, medical meshes were made as knitted or woven fabrics in which interstices were naturally formed at places where filament came into contact or close proximity. These interstices can harbor bacteria, which can be small enough to enter the interstices while keeping white blood cells out because the white cells can be too large to enter the interstices. This can lead to severe infections and mesh removal surgery. The methods of depositing adhesive material in the regions where filament meets provided for in the present disclosure allows the interstices to be eliminated by being filled with the adhesive or another material. The ability to create a fabric in a non-woven matter that is devoid of interstices at locations where filaments are bonded together is a useful development made possible by the present disclosure.

Additionally, the fibers can be bonded, patterned, or interwoven at selected points to produce desired mechanics that allow for the production of a fabric or a material with fabric-like mechanics. In some embodiments, meshes can feature filament orientation that is organized (not random) to provide mechanical strength, flexibility, deformation, toughness, robustness in different direction, and other properties (e.g., electrical or thermal conductivity). The intersection locations of the filaments can be bonded together non-stochastically and rationally with respect to a volume of the resulting object (e.g., medical textile, medical implant, garment, clothing). As described throughout the present application, properties of the resulting non-woven fabric can be impacted by changing a patterning of at least one of the filaments of the plurality of filaments and an adhesive used in conjunction with the plurality of filaments, with respect to other filaments of the plurality of filaments or other adhesives used in conjunction with the plurality of filaments. Likewise, properties of the resulting non-woven fabric can be impacted by changing a composition of at least one of the filaments of the plurality of filaments and an adhesive used in conjunction with the plurality of filaments in a first region of the fabric while not necessarily changing a composition of at least one of the filaments of the plurality of filaments and an adhesive used in conjunction with the plurality of filaments in a second region of the fabric.

The mesh 150' of FIG. 5B does not generally include any local variations. Instead each of the interlayer nodes are bonded together. The nodes 118' are the location of intersection between the filaments. Characteristics of the mesh, such as pore size, can be varied to customize the fit of the mesh. In the illustrated embodiment, the pores 156' are each of the spaces disposed between the crossed filaments of the mesh 150'. The mesh 150" of FIG. 5C, on the other hand, includes a local variation in which a central region 152" in which the interlayer nodes are not bonded together, while a peripheral region 154" includes interlayer nodes that are bonded together. In each illustration, a same weight 170 is disposed at an end 150e', 150e". As illustrated, the mesh 150' having interlayer node bonding throughout the mesh, and thus in a central region, is less deformed than the mesh 150" in which the central region 152" is devoid of interlayer node bonding. This demonstrates that interlaying node bonding provides desirable strength without unwanted deformation of the mesh. The embodiment of the mesh 150 of FIG. 5A is thus particularly advantageous because it provides for a central region 152 that provides the desired strength and stiffness due to the interlayer node bonding, while also allowing for flexibility in the other regions by not providing interlayer bonding. The additional flexibility on the peripheral region 154 can minimize discomfort because the mesh is more conformable and less rigid in the peripheral region.

The illustrations of FIGS. 5A-5E demonstrate that by locally adjusting at least one of an orientation, thickness, and composition of the filament(s) and the adhesive(s) used in conjunction with the deposited filament as described herein, the resulting fabric can have a varied mechanical response to application of an outside force across a surface area of the fabric. Local adjustments provided for herein include but are not limited to: (1) modulating shear stress of the fabric by changing interfilament bonding; (2) modulating out-of-plane extension of the fabric in response to in-plane compression or tension of the fabric; (3) modulating tensile stiffness of the fabric through localized filament slack; and (4) modulating Poisson's ratio through filament and bonding patterns. Further, modulating adhesion of the filament controls a shear modulus of the fabric. This can be particularly useful for meshes, such as those used to repair hernias, because it controls the forces experienced by the wound during healing, and thus helps determine surgery outcomes.

Further benefits of the resulting objects (e.g., medical textiles, medical implants, garments, clothing) are that when the object is laid out on a non-planar surface, the object conforms to the surface. Thus, no folds or wrinkles occur in the object. This is due, in part, to the ability to vary the properties of the resulting object across its surface area. Still further, filament or fiber printed in conjunction with the systems, devices, and methods provided for herein can have an axial tensile strength that is greater than known 3D printing techniques, such as FDM, SLS, and stereolithography. For example, the axial tensile strength can be greater than about 150 MPa.

In an exemplary embodiment, the in-plane stiffness of a mesh can be tuned by a factor of 3. Additionally, the displacement at which the stiffening occurs can be specified by modulating the bonding at interfilament nodes. This enables control of stiffness, pore size, and load capacity by introducing local slack into the filaments in a given area of the mesh, and controlling the diameter, density, and orientation of filament. By way of non-limiting example, the present disclosures allow for filament or fiber density of a resulting fabric to be less than or equal to an amount that produces a pore size of 4 mm. Printing onto a 3D template can also be enabled so that the fabric conformably matches a desired surface (e.g., a 3D printed model of a patient's organ). Additionally, the surface area of the implant can be reduced by replacing knots and loops with straight monofilament. The use of loops in knitted mesh results in very high local surface area that leads to excessive foreign body reaction and tissue weakening. These loops also present microvoids large enough for bacteria to penetrate, but too small for white blood cells to reach, preventing the elimination of the bacteria from the body. Mesh having larger pores, as disclosed herein, can lead to less foreign body reaction, and having a mesh with the same stiffness as healthy tissue can lead to healthier tissue ingrowth. In some embodiments, the mesh can contain no loops due to knitting, which can result in fewer microvoids or interstices. The absence of loops can allow the mesh to have a larger pore size, which helps with tissue integration. The absence of loops also allows for the use of larger diameter filament in the mesh while achieving the same flexibility because each filament does not need to be as highly deformed to produce a desired mesh deformation. This can further reduce the needed surface area of an implant.

The local control of mechanics in 3D printed surgical mesh to mirror body mechanics as well as the customized conformity of a 3D printed hernia mesh can improve significantly on existing meshes, for example in reducing the incidence of chronic pain after implantation as well as other complications. Further, modulating properties such as the microvoids or interstices between the nodes, the pore size distribution of the mesh, and the porosity can improve ingrowth of a patient's tissue and result in healthier tissue after surgery. In some embodiments, other mechanical responses of the mesh can be manipulated, e.g., tensile stiffness in different directions, tensile shear stiffness, and flexural stiffness. In additional embodiments, the geometry of the mesh, e.g., its 3D curvature and porosity, can also be manipulated. These mechanical responses can then be customized to fit the underlying tissue. Material composition can also be tuned throughout the implant to change properties including absorption by the patient. In some embodiments, the implant can include a non-absorbable filament such as polypropylene in some parts, which can provide long-term mechanical support, while other parts can include an absorbable polymer such as polylactic acid or polyglycolic acid for providing temporary support. The mechanical support provided by the implant can be spatially and temporally planned to maximize comfort and reinforcement while minimizing complications. In some embodiments, the mesh can be composed of different substances e.g., conductive, elastic, high-strength, or drug eluting materials, to produce meshes with varying functionality.

By 3D printing, the part can also be customized through tailoring the geometry and mechanics using information found about a patient through computed tomography or ultrasound imaging. Such customization is can be important for complex meshes used in operations such as repairing pelvic organ prolapse or stress urinary incontinence where complication rates are currently very high. In some embodiments, the mesh can include dense filament over the hole to be patched itself, while the remainder of the part can be much less dense and shaped such that it simply maintains the part covering the hole in place via hooks or similar attachment devices.

Further, if bacteria come into contact with the implanted mesh, they can attach themselves and multiply, forming a biofilm that protects from antibiotics. Existing mesh can also exacerbate recurrence, chronic pain, and infection. Surgical meshes are typically flat and have uniform mechanical stiffness, while the tissues they are intended to support feature great variation in curvature, stiffness, and direction of motion. This mismatch leads to stress concentrations and shear forces that cause mesh folding and displacement, while preventing the conversion of stiff scar tissue into tough, healthy tissue. Both extensive stitching and large mesh overlap around the site of operation are needed to keep the mesh in place, further damaging the tissue. Small pores magnify chronic pain/discomfort as scars will fuse into a large, palpable mass. Further, the uniform density of the mesh, even in areas that only provide overlap or an anchor, contributes to scar tissue formation and patient discomfort without providing useful support.

While the medical implant primary described herein is a mesh, a person skilled in the art will recognize that many other types of medical implants can also be produced in view of the present disclosures. By way of non-limiting example, stents are another medical implant that can benefit from the present disclosures. The stents can also be customized such that the stents expand or contract into a pre-determined shape and/or in different directions using local control of mechanical responses such as Poisson's ratio and stent composition. The use of auxetic materials to make the stents can particularly help the stent expand in different directions and therefore to direct blood flow in complex vascular geometries. The disclosures provided that allow for localized adjustment of the properties of a mesh can likewise allow for localized adjustment of the properties of a stent, i.e., different portions of the stent can be manufactured to adjust the strength and flexibility as desired, and to include other properties (e.g., drug-eluting) based on the way the stent is manufactured and the materials used to manufacture it. Other implants with which the present disclosures can be used include but are not limited to implants used in conjunction with organs and muscles generally, and breasts and abdomens more specifically. Accordingly, a person skilled in the art will be able to manufacture breast implants and abdomen implants to provide the desired support. For example, an implant for use with a breast can provide for a desired stiffness under the breast and/or over the breast, depending on the desired location of the implant. When used in conjunction with muscles, a person skilled in the art can create an implant having a first region of stiffness over certain muscle tissue and a second region of stiffness over other portions of the muscle tissue, with one of the regions having less stiffness in the direction of contraction of the muscle. In accordance with the present disclosures, a region of stiffness can be achieved across any portion of an implant, whether at the edges, in a central location, or otherwise, and/or in different orientations. The stiffness can be modulated, for example, by the orientation of the filaments and/or the modulation of bonding strength at the intersection nodes. As a result, in some instances, the resulting object or implant can include support structures designed to have stiffer regions to provide added support where needed. Additional support and strength can be provided by layering additional filaments at one location and not at others.

More broadly, the present disclosures are also by no means limited to medical implants. Any object involving fabric can be printed using the systems, devices, and methods provided for herein. A person skilled in the art could easily apply the present disclosures to manufacturing apparel, other types of medical implants, and in general most any object in which a fabric is used. Generally, the present disclosures are advantageous for any fabric because traditional fabrics that are woven or knitted have the same density across a surface area because otherwise it would typically unravel, while the present disclosures allows material to be deposited only where it is needed, so there is not necessarily a uniform density. Still further, these techniques can also be applied outside of objects having fabric, and can be more broadly applied to any 3D printing technique.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A method for printing a surgical mesh or brace in three dimensions, the method comprising:
forming a three-dimensional template based on one or more structures of an anatomy of a patient;
depositing a filament onto at least one of a surface of the template or one or more previously deposited filaments on the three-dimensional template to form a multi-layered structure that conformably matches a shape of the three-dimensional template, said depositing taking place from one nozzle of a combination of warp nozzles and weft nozzles configured to advance along at least a first and second path, respectively; and
selectively modulating adhesion of the filament being deposited to the at least one of the surface or the one or more previously deposited filaments across a length of the filament being deposited to form a fabric such that some interfaces between the filament being deposited and the at least one of the surface or the one or more previously deposited filaments are bonded together at these some interfaces while some other interfaces between the filament being deposited and the at least one of the surface or the one or more previously deposited filaments are unbonded at these other interfaces.

2. The method of claim 1, wherein selectively modulating adhesion of the filament being deposited further comprises performing photopolymerization on a bonding agent that is in contact with the filament being deposited.

3. The method of claim 1, wherein selectively modulating adhesion of the filament being deposited further comprises at least one of: (1) bringing the filament being deposited into contact with the at least one of the surface and the one or more previously deposited filaments; (2) controlling a rate at which a solvent associated with the filament being deposited evaporates prior to the filament being deposited coming into contact with the at least one of the surface and the one or more previously deposited filaments; (3) selectively exposing regions that include one or more filament interstices before, during, or after said depositing of the filament to one or more of light able to cure a photopolymer applied to the filament being deposited, or a material having light-responsive bonding agents associated therewith; (4) selectively exposing regions that include one or more filament interstices to heat before, during, or after said depositing of the filament; (5) selectively using an adhesive at regions that include one or more filament interstices during or after said depositing of the filament; or (6) selectively using an adhesive to provide bonding between the filament being deposited and the one or more previously deposited filaments.

4. The method of claim 1, further comprising:
depositing one or more additional filaments onto at least one of the surface or the one or more previously deposited filaments; and
selectively modulating adhesion of the one or more additional filaments being deposited to the at least one of the surface or the one or more previously deposited filaments across a length of the one or more additional filaments being deposited such that some interfaces between the one or more additional filaments being deposited and the at least one of the surface or the one or more previously deposited filaments are bonded together at these some interfaces while some other interfaces between the one or more additional filaments being deposited and the at least one of the surface or the one or more previously deposited filaments are unbonded at these other interfaces.

5. The method of claim 4, further comprising locally adjusting at least one of an orientation, thickness, or composition of at least one of: (a) the one or more previously deposited filaments or the one or more additional filaments, or (b) one or more adhesives used in conjunction with the one or more previously deposited filaments or the one or more additional filaments, the locally adjusting action resulting in the fabric having a varied mechanical response to application of an outside force across a surface area of the fabric.

6. The method of claim 5, wherein locally adjusting at least one of an orientation, thickness, or composition of at least one of: (a) the one or more previously deposited filaments or the one or more additional filaments, or (b) one or more adhesives used in conjunction with the one or more previously deposited filaments or the one or more additional filaments further comprises at least one of: (1) modulating shear stress of the fabric by changing interfilament bonding; (2) modulating out-of-plane extension of the fabric in response to in-plane compression or tension of the fabric; (3) modulating tensile stiffness of the fabric by modulating localized filament slack; or (4) modulating Poisson's ratio by modulating filament and bonding patterns.

7. The method of claim 4, wherein depositing one or more additional filaments onto at least one of the surface or the one or more previously deposited filaments occurs from one or more additional nozzles of the combination of warp nozzles and weft nozzles.

8. The method of claim 1, wherein the fabric has a varied mechanical response that results from a configuration of the fabric in which a first region across the surface area of the fabric has smaller pores formed between the filament being deposited and the one or more previously deposited filaments than pores formed between the filament being deposited and the one or more previously deposited filaments of a second region across the surface area of the fabric.

9. The method of claim 1, wherein selectively modulating adhesion of the filament being deposited controls one or more of the following fabric properties: deformation, electrical conductivity, thermal conductivity, or toughness.

10. The method of claim 1, wherein the material of the filament being deposited and the one or more previously deposited filaments, or one or more adhesives used in conjunction with the filament being deposited and the one or more previously deposited filaments, comprises at least one of a thermoplastic polymer or a thermoset polymer.

11. The method of claim 1, wherein the filament being deposited and an adhesive used in conjunction with the filament being deposited comprise the same material.

12. The method of claim 1, further comprising:
dissolving a polymer in a solvent to form a viscous fluid, wherein depositing a filament onto at least one of a surface or one or more previously deposited filaments further comprises extruding the viscous fluid through the one nozzle of the warp and weft nozzles to form the filament being deposited.

13. The method of claim 12, wherein extruding the viscous fluid through the one nozzle to form the filament being deposited further comprises:
positioning the nozzle at a first location with respect to the at least one of a surface or one or more previously deposited filaments;
depositing an initial portion of the filament being deposited from the nozzle at a first site on the at least one of a surface or one or more previously deposited filaments;
moving the nozzle to a second location with respect to the at least one of a surface or one or more previously deposited filaments while depositing an additional portion of the filament being deposited from the nozzle towards the at least one of a surface or one or more previously deposited filaments so as to stretch the additional portion of the filament being deposited;
positioning the nozzle at a third location with respect to the at least one of a surface or one or more previously deposited filaments; and
depositing an end portion of the filament being deposited from the nozzle at a second site on the at least one of a surface or one or more previously deposited filaments.

14. The method of claim 13, wherein moving the nozzle to a second location further comprises raising the nozzle to the second location with the second location being above the first location with respect to the at least one of the surface or the one or more previously deposited filaments.

15. The method of claim 14, wherein raising the nozzle to the second location further comprises accelerating the nozzle.

16. The method of claim 13, further comprising accelerating the nozzle after positioning the nozzle at the third location so as to straighten the additional portion of filament.

17. The method of claim 13, wherein the first and third locations are proximate to the surface.

18. The method of claim 1, wherein selectively modulating adhesion of the filament being deposited controls a shear modulus of the fabric.

19. The method of claim 1, wherein the surface is an adhesive surface.

20. The method of claim 1, wherein the filament being deposited is compromised of at least one of: a continuous, pre-made filament, an adhesive-coated filament, or an adhesive filament.

21. The method of claim 1, wherein selectively modulating adhesion of the filament being deposited occurs during the step of depositing a filament onto the at least one of the surface or the one or more previously deposited filaments.

22. The method of claim 1, wherein the fabric is devoid of interstices at these some interfaces.

23. The method of claim 1, wherein selectively modulating adhesion of the filament being deposited occurs on a layer-by-layer basis.

24. The method of claim 1, further comprising imaging the one or more structures of the anatomy of the patient from which the three-dimensional template is formed.

25. A method for printing a surgical mesh or brace in three dimensions, the method comprising:
    forming a three-dimensional template based on one or more structures of an anatomy of a patient;
    positioning a nozzle at a first location with respect to at least one of a surface of the template or one or more previously deposited filaments, the nozzle being one nozzle of a combination of warp nozzles and weft nozzles configured to advance along at least first and second paths, respectively;
    depositing a thermoplastic filament from the one nozzle to form a multi-layered fabric conformably matching a shape of the three-dimensional template, said depositing taking place by:
        extruding an initial portion of thermoplastic filament from the nozzle at a first site of the at least one of the surface or the one or more previously deposited filaments on the three-dimensional template;
        moving the nozzle to a second location with respect to the at least one of the surface or the one or more previously deposited filaments while extruding an additional portion of the thermoplastic filament from the nozzle towards the at least one of the surface or the one or more previously deposited filaments so as to stretch the additional portion of the filament being deposited, the second location being above the first location with respect to the at least one of the surface or the thermoplastic filament that has been extruded such that said moving the nozzle to the second location includes raising the nozzle, and the nozzle accelerating during movement to the second location;
        positioning the nozzle at a third location with respect to the at least one of the surface or the one or more previously deposited filaments; and
        extruding an end portion of the thermoplastic filament from the nozzle at a second site of the at least one of the surface or the one or more previously deposited filaments.

26. The method of claim 25, further comprising selectively modulating adhesion of the thermoplastic filament being extruded on the at least one of the surface or the one or more previously deposited filaments.

27. The method of claim 26, wherein selectively modulating adhesion of the thermoplastic filament being extruded occurs during said extrusion of the thermoplastic filament.

28. The method of claim 26, wherein selectively modulating adhesion of the thermoplastic filament being extruded further comprises at least one of: (1) bringing the thermoplastic filament being extruded into contact with the at least one of the surface and the one or more previously deposited filaments; (2) controlling a rate at which a solvent associated with the thermoplastic filament being extruded evaporates prior to the thermoplastic filament being extruded coming into contact with the at least one of the surface and the one or more previously deposited filaments; (3) selectively exposing regions that include one or more filament interstices before, during, or after said depositing of the filament to one or more of light able to cure a photopolymer applied to the filament being deposited, or a material having light-responsive bonding agents associated therewith; (4) selectively exposing regions that include one or more filament interstices to heat before, during, or after said depositing of the thermoplastic filament; (5) selectively using an adhesive at regions that include one or more filament interstices during or after said depositing of the thermoplastic filament; or (6) selectively using an adhesive to provide bonding between the thermoplastic filament being extruded and the one or more previously deposited filaments.

29. The method of claim 26, further comprising:
    positioning the nozzle with respect to the at least one of a surface or one or more previously deposited filaments;
    extruding one or more additional thermoplastic filaments from the nozzle;
    moving the nozzle to another location with respect to the at least one of the surface or the one or more previously deposited filaments while extruding a portion of the one or more additional thermoplastic filaments from the nozzle towards the at least one of the surface or the one or more previously deposited filaments so as to stretch the portion of the one or more additional thermoplastic filaments, the another location being above the location at which extrusion of the one or more additional thermoplastic filaments began such that said moving the nozzle includes raising the nozzle, and the nozzle accelerating during movement to the another location; and
    extruding an end portion of the one or more additional thermoplastic filaments from the nozzle on the at least one of the surface or the one or more previously deposited filaments.

30. The method of claim 26, further comprising:
    dissolving a thermoplastic polymer in a solvent to form a viscous fluid,
    wherein said extruding of an initial portion of a thermoplastic filament from the nozzle at a first site of the at least one of the surface or one or more previously deposited filaments further comprises extruding the viscous fluid through the nozzle to form the thermoplastic filament being extruded.

31. The method of claim 25, further comprising imaging the one or more structures of the anatomy of the patient from which the three-dimensional template is formed.

32. The method of claim 25, further comprising:
positioning one or more additional nozzles of the combination of warp nozzles and weft nozzles with respect to the at least one of a surface or one or more previously deposited filaments;
extruding one or more additional thermoplastic filaments from the one or more additional nozzles;
moving the one or more additional nozzles to another location with respect to the at least one of the surface or the one or more previously deposited filaments while extruding a portion of the one or more additional thermoplastic filaments from the one or more additional nozzles towards the at least one of the surface or the one or more previously deposited filaments so as to stretch the portion of the one or more additional thermoplastic filaments, the another location being above the location at which extrusion of the one or more additional thermoplastic filaments began such that said moving the one or more additional nozzles includes raising the one or more additional nozzles, and the one or more additional nozzles accelerating during movement to the another location; and
extruding an end portion of the one or more additional thermoplastic filaments from the one or more additional nozzles on the at least one of the surface or the one or more previously deposited filaments.

* * * * *